United States Patent
Li

(10) Patent No.: US 9,585,929 B2
(45) Date of Patent: Mar. 7, 2017

(54) COIX SEED OIL CONTAINING 13 GLYCERIDES, AND PHARMACEUTICAL PREPARATION AND USE THEREOF

(71) Applicant: ZHEJIANG KANGLAITE GROUP CO., LTD., Hangzhou, Zhejiang (CN)

(72) Inventor: Dapeng Li, Zhejiang (CN)

(73) Assignee: ZHEJIANG KANGLAITE GROUP CO., LTD., Xiasha Economic and Technological Development Zone, Hangzhou, Zhejiang (CN)

( * ) Notice: Subject to any disclaimer, the term of this patent is extended or adjusted under 35 U.S.C. 154(b) by 0 days.

(21) Appl. No.: 14/733,079

(22) Filed: Jun. 8, 2015

(65) Prior Publication Data
US 2016/0015769 A1      Jan. 21, 2016

(30) Foreign Application Priority Data

Jul. 18, 2014   (CN) .......................... 2014 1 0342342

(51) Int. Cl.
| | | |
|---|---|---|
| *A01N 37/02* | (2006.01) | |
| *A61K 36/8994* | (2006.01) | |
| *A61K 31/232* | (2006.01) | |
| *A61K 31/231* | (2006.01) | |

(52) U.S. Cl.
CPC ........ *A61K 36/8994* (2013.01); *A61K 31/231* (2013.01); *A61K 31/232* (2013.01); *A61K 2236/00* (2013.01)

(58) Field of Classification Search
USPC ....................................................... 514/547
See application file for complete search history.

(56) References Cited

U.S. PATENT DOCUMENTS 8,911,800 B2 * 12/2014 Tseng ................. A61K 36/8994
                                                                    424/725

OTHER PUBLICATIONS

Hu et al. Study Progress of Coix Seed. Lishizhen Medicine and Materia Medica Research 2009 vol. 20 No. 5, 1059-1060.*
Li Faming Zhuanli Shenqing Gongkai Shuomingshu (2004), CN 148541).*
Yu feng et al. Dalton Institute of Chemical Physics, Academia Sinica, 1166012, 1990, p. 379-382.*
Zhong et al. Journal of Chinese Medicinal Materials, 2008, 31(11), 1613-1614.*

* cited by examiner

*Primary Examiner* — Nizal Chandrakumar
(74) *Attorney, Agent, or Firm* — Global IP Services; Tianhua Gu

(57) ABSTRACT

The present invention relates to *Coix* seed oil extracted from *Semen Coicis*, pharmaceutical preparations thereof, and the use thereof in the treatment of tumors and inflammation. Specifically, the *Coix* seed oil contains 5 diglyceride and 8 triglyceride ingredients in the following mass percentages: 1,3-diolein 0.40-0.58%, 1-linolein-3-olein 0.91-1.31%, 1,2-diolein 0.24-0.35%, 1-olein-2-linolein 0.66-0.95%, 1,2-dilinolein 0.33-0.47%, trilinolein 4.87-6.99%, 1-olein-2,3-dilinolein 13.00-18.69%, 1-palmitin-2,3-dilinolein 5.25-7.54%, 1,3-diolein-2-linolein 13.23-19.02%, 1-palmitin-2-linolein-3-olein 10.26-14.75%, 1,3-dipalmitin-2-linolein 2.28-3.28%, triolein 14.44-20.76% and 1-palmitin-2,3-diolein 8.06-11.58%.

13 Claims, No Drawings

COIX SEED OIL CONTAINING 13 GLYCERIDES, AND PHARMACEUTICAL PREPARATION AND USE THEREOF

CROSS REFERENCE TO RELATED PATENT APPLICATION

The present application claims a priority of the Chinese patent application CN201410342342.1 with filing date Jul. 18, 2014, which application is incorporated herein by reference.

FIELD OF THE INVENTION

The present invention relates to the pharmaceutical field, specifically, the present invention relates to *Coix* seed oil, pharmaceutical preparations thereof, the process for the preparation of same and the use thereof in the treatment of tumors and inflammation.

BACKGROUND OF THE INVENTION

*Coix* seeds are dried ripe seeds of *Coix lacryma-jobi* L. var *ma-yuen* (Roman.), *Stapf*, a genus of plant in the Poaceae family. It is a dampness-eliminating drug and has been used as a medicinal and edible plant for a long time. Modern researches have found that *Coix* seeds have many pharmacological effects, such as analgesic anti-inflammatory, immunomodulatory, anti-ulcer, hypolipidemic and anti-obesity effects. In recent years, researchers around the world have studied the chemical composition of the *Coix* seed by using TLC, HPLC-MS, GC, etc., and found a variety of active ingredients in it, including coixenolide, triglycerides, fatty acids, lactams, *coix* lactones, saccharides, sterols and triterpenoids. Among them, esters are the first discovered components having anti-tumor activities and the most reported chemical composition attracting the most attention. Kanglaite injection, in which the active ingredient is *Coix* seed oil, has been widely used in present Chinese clinical applications, but the *Coix* seed oil used in the Kanglaite injection comprises complex components. In addition to triglycerides, it also contains monoglycerides, diglycerides and fatty acid esters, etc. This will inevitably be a great challenge for the quality control in the practical production process and the safety in clinical applications.

In the present invention, the raw material *Coix* seed powder underwent supercritical carbon dioxide extraction, basification, neutral alumina purification and kaolin purification, etc., to afford an effective part, *Coix* seed oil. With the active ingredients' isolation and identification, it is determined that the *Coix* seed oil comprises mainly eight triglyceride components and 5 diglyceride components. Further determination of physicochemical constants has confirmed the optimal acid value, iodine value, saponification value, refractive index and specific gravity, etc. The use of the *Coix* seed oil of the invention in medication has advantages such as the confirmed composition of ingredients, ensuring quality stability in every batch in the industrial production.

SUMMARY OF THE INVENTION

The first aspect of the invention is to provide a *Coix* seed oil extracted from *Semen Coilis*. The *Coix* seed oil contains 5 diglyceride and 8 triglyceride ingredients in the following mass percentages: 1,3-diolein 0.40-0.58%, 1-linolein-3-olein 0.91-1.31%, 1,2-diolein 0.24-0.35%, 1-olein-2-linolein 0.66-0.95%, 1,2-dilinolein 0.33-0.47%, trilinolein 4.87-6.99%, 1-olein-2,3-dilinolein 13.00-18.69%, 1-palmitin-2,3-dilinolein 5.25-7.54%, 1,3-diolein-2-linolein 13.23-19.02%, 1-palmitin-2-linolein-3-olein 10.26-14.75%, 1,3-dipalmitin-2-linolein 2.28-3.28%, triolein 14.44-20.76% and 1-palmitin-2,3-diolein 8.06-11.58%.

Preferably, mass percentage contents of the above 5 diglyceride and 8 triglyceride ingredients are: 1,3-diolein 0.45-0.55%, 1-linolein-3-olein 1.03-1.25%, 1,2-diolein 0.27-0.33%, 1-olein-2-linolein 0.75-0.91%, 1,2-dilinolein 0.37-0.45%, trilinolein 5.47-6.69%, 1-olein-2,3-dilinolein 14.63-17.88%, 1-palmitin-2,3-dilinolein 5.90-7.21%, 1,3-diolein-2-linolein 14.88-18.19%, 1-palmitin-2-linolein-3-olein 11.55-14.11%, 1,3-dipalmitin-2-linolein 2.57-3.14%, triolein 16.25-19.86% and 1-palmitin-2,3-diolein 9.07-11.08%.

More preferably, mass percentage contents of the above 5 diglyceride and 8 triglyceride ingredients are: 1,3-diolein 0.49-0.51%, 1-linolein-3-olein 1.12-1.16%, 1,2-diolein 0.29-0.31%, 1-olein-2-linolein 0.81-0.85%, 1,2-dilinolein 0.40-0.42%, trilinolein 5.96-6.20%, 1-olein-2,3-dilinolein 15.93-16.58%, 1-palmitin-2,3-dilinolein 6.43-6.69%, 1,3-diolein-2-linolein 16.20-16.87%, 1-palmitin-2-linolein-3-olein 12.57-13.09%, 1,3-dipalmitin-2-linolein 2.79-2.91%, triolein 17.69-18.42% and 1-palmitin-2,3-diolein 9.87-10.27%.

The above contents refer to the mass percentage contents of diglyceride and triglyceride compounds in the *Coix* seed oil. 5 diglyceride and 8 triglyceride monomer compounds can be separated by using preparative chromatography from the *Coix* seed oil prepared by the following steps, and their contents can be obtained by weighing and calculating the products. They can also be obtained according to conventional analytic methods in the art.

The *Coix* seed oil has the following physicochemical constants based on the fatty oils: specific gravity at 20 0.916-0.920, refractive index at 20° C. 1.471-1.474, acid value<0.2, iodine value 100-106, saponification value 186-195.

The *Coix* seed oil of the invention can be prepared by a refining process of crude *Coix* seed oil extracted by supercritical carbon dioxide extraction, wherein:

the process of the supercritical carbon dioxide extraction comprises steps of:

crushing *Coix* seeds into 10 mesh-80 mesh powder and extracting same using a supercritical $CO_2$ extraction system in which *Coix* seed powder is put in 600 L×2 extractors; the $CO_2$ preheater, extractor and separation column are heated by jacketed circulating hot water to make the extraction temperature and separation temperature to reach 33-45° C. and 30-45° C., respectively; the outlet temperatures of separator I and separator II are kept at 20-50° C. and 15-35° C., respectively; the liquid $CO_2$ is pressed at a flow rate of 1-3 t/h into the $CO_2$ preheater via a high pressure pump, turning into a fluid in supercritical state; in the extractor, an oil is extracted into the $CO_2$ fluid at a pressure of 19-23 Mpa; then the $CO_2$ fluid with this oil enters the separation column in which the pressure is controlled to 7-10 Mpa to separate this oil; the $CO_2$ gas out from the separation column enters sequentially into separator I and separator II in which the pressure is sustained at 5-7 Mpa and 4-6 Mpa, respectively; impurities such as water separated therefrom are discarded; the $CO_2$ gas returns to liquid $CO_2$ for reuse through a condenser; and a continuous extraction for 2-3 h affords the crude *Coix* seed oil; and the refining process comprises steps of:

adding petroleum ether (bp. 60° C.-90° C.) into the *Coix* seed oil obtained by the supercritical $CO_2$ extraction in an amount of 60% of the oil weight; adding 2% NaOH aqueous solution in an amount ranging from 36% to 56% of the oil weight according to the acid value; after stirring the mixture for 10 min and standing for 18-24 h, removing the lower niger layer; washing the upper layer with purified water and letting stand for 18-24 h; after the removal of the lower waste water, washing the upper layer again; after another standing for 40-50 h, removing the lower waste water; and demulsifying the upper layer with acetone in an amount of 70%-90% of the oil weight; after standing for 2-4 h, removing the lower waste acetone and adding 3% to 8% of activated neutral alumina by weight of crude oil in the upper oil layer; stirring the mixture for 30 min, then filtering off the precipitation; heating the filtrate and adding 2% to 6% of activated kaolin by weight of crude oil; stirring the mixture for 30 min at 40-50° C. and then filtering off the precipitation; concentrating the filtrate under a reduced pressure to recover the solvent, then washing again with purified water; after standing for 1-2 h, removing the lower waste water and heating the upper oil layer and vacuum drying it under nitrogen atmosphere; then adding 8 to 12% activated neutral alumina by weight of crude oil and stirring the mixture and allowing to stand at a cold place; after filtrating, concentrating the filtrated oil via heating under vacuum in a nitrogen atmosphere and sterilizing the oil via dry heat sterilization under vacuum at 160-170° C. for 1-2 h; after cooling, filtering the oil through a 0.2 μm microporous membrane; then split charging the obtained *Coix* seed oil in 500 mL glass infusion bottles, nitrogenizing and sealing the bottles.

Preferably, the refining process comprises steps of:

adding petroleum ether (bp. 60° C.-90° C.) into the *Coix* seed oil obtained by the supercritical $CO_2$ extraction in an amount of 60% of the oil weight; adding 2% NaOH aqueous solution in an amount ranging from 36% to 56% of the oil weight according to the acid value; after stirring the mixture for 10 min and standing for 20 h, removing the lower niger layer; washing the upper layer with purified water and letting stand for 22 h; after the removal of the lower waste water, washing the upper layer again; after standing for another 46 h, removing the lower waste water; demulsifying the upper layer with acetone in an amount of 70%-90% by weight of the crude oil and standing for 3 h; removing the lower waste acetone and adding 5% of activated neutral alumina by weight of crude oil in the upper oil layer; stirring the mixture for 30 min, then filtering off the precipitation; heating the filtrate, and adding 4% of activated kaolin by weight of crude oil; stirring the mixture for 30 min at 40-50° C., and then filtering off the precipitation; concentrating the filtrate under a reduced pressure to recover the solvent, then washing again with purified water; after standing for 1 h, removing the lower waste water; heating the upper oil layer and vacuum drying it in nitrogen atmosphere; then adding 8%-12% activated neutral alumina, stirring the mixture and allowing to stand at a cold place; after filtration, concentrating the filtrated oil via heating under vacuum in a nitrogen atmosphere and sterilizing the concentrated oil via dry heat sterilization under vacuum at 160-170° C. for 2 h; after cooling, filtering the oil through a 0.2 μm microporous membrane; then split charging the obtained *Coix* seed oil in 500 mL glass infusion bottles, nitrogenizing and sealing the bottles.

The *Coix* seed oil of the invention is a yellowish clear liquid with a light odor and a light taste. It is highly soluble in petroleum ether or chloroform, freely soluble in acetone, slightly soluble in ethanol, but insoluble in water.

The *Coix* seed oil prepared based on the above methods was detected according to the method in the appendix of "Pharmacopoeia of the People's Republic of China" (2010 edition) Volume I. Physicochemical constants thereof are: specific gravity at 20 0.916-0.920, refractive index at 20° C. 1.471-1.474, acid value<0.2, iodine value 100-106, saponification value 186-195. The acid value according to the Pharmacopoeia refers to the weight of potassium hydroxide (in milligrams) needed to neutralize free fatty acids contained in 1 gram of fats, fatty oils, or other similar substances. In the quality study of oil products, acid value is an important evaluation. As far as the *Coix* seed oil of the invention, the acid value is less than 0.2. By the optimization of the preparation process such as supercritical extraction parameters and the purification process like basification, *Coix* seed oil was prepared with the following advantages: on the one hand, it has a very low content of free fatty acid impurities, which means a high product quality; on the other hand, it gathers a great amount of active ingredients of diglycerides and triglycerides in high purity, and the types of diglycerides and triglyceride ingredients therein are determinate, and the contents thereof are stable. In addition, other physicochemical constants, such as saponification value, iodine value, etc., measured between batches of samples, had a small range of variation. It further illustrates that the *Coix* seed oil of the invention has a stable quality and a safer clinical use. The preparation method of the invention gives a stable product with a high yield and a low cost. It is suitable for the industrial production in view of the safety and controllability.

The second aspect of the invention is to provide a pharmaceutical preparation containing *Coix* seed oil, specifically, it comprises a therapeutically effective amount of the *Coix* seed oil of the invention and one or more pharmaceutically acceptable carriers.

Pharmaceutically acceptable carriers can be selected from pharmaceutical conventional dilutions, excipients, fillers, emulsifiers, binders, lubricants, absorption accelerators, surfactants, disintegrants, lubricants and antioxidants, if necessary, flavoring agents, sweeteners, preservative and/or coloring agents Pharmaceutically acceptable carriers can be selected from one or more in the group consists of: mannitol, sorbitol, sodium metabisulfite, sodium bisulfite, sodium thiosulfate, cysteine hydrochloride, thioglycolic acid, methionine, soybean lecithin, vitamin C, vitamin E, EDTA disodium, EDTA calcium sodium, monovalent alkali metal carbonate, acetate, phosphate or its aqueous solution, hydrochloric acid, acetic acid, sulfuric acid, phosphoric acid, amino acids, sodium chloride, potassium chloride, sodium lactate, ethylparaben solution, benzoic acid, potassium sorbate, chlorhexidine acetate, xylitol, maltose, glucose, fructose, dextran, glycine, starch, sucrose, lactose, mannitol, silicic derivatives, cellulose and its derivatives, alginates, gelatin, polyvinyl pyrrolidone, glycerin, Tween 80, agar-agar, calcium carbonate, calcium bicarbonate, surfactants, polyethylene glycol, cyclodextrin, β-cyclodextrin, phospholipid material, kaolin, talc, and calcium stearate or magnesium stearate.

Pharmaceutical preparation can be oral solid preparations, oral liquid preparations or injections.

Preferably, the oral solid preparation is selected from any one of capsules, tablets, dripping pills, granules, and concentrated pills; the oral liquid preparation is selected from any one of aqueous or oily suspensions, solutions, emulsions, syrups or elixirs, and a dry product that may be reconstructed by water or other suitable carrier before use; and the injection is selected from any one of nano suspensions, liposomes, emulsions, lyophilized powder for injection and aqueous injection.

More preferably, the injection comprises the following components: the *Coix* seed oil of the invention 50-350 g, soybean lecithin for injection or soybean lecithin acceptable for injection 10-40 g, glycerin for injection or glycerin acceptable for injection 15-50 g, and water for injection adds to 1000 mL.

The injection of the invention can be prepared by a method comprising steps of:

adding appropriate amount of water for injection to a formulated amount of soybean lecithin for injection or soybean lecithin acceptable for injection; dispersing the mixture with a high shear dispersing emulsifier to give a dispersion without bulks or granules; adding a formulated amount of glycerin for injection or glycerin acceptable for injection; then adding water for injection to a specified amount, and stirring the mixture to give a water phase;

weighing a formulated amount of *Coix* seed oil; heating the weighed oil and the water phase separately to 60-70° C., then mixing them and emulsifying the mixture in a high pressure homogenizer, in which the low pressure is 5-12 MPa and the high pressure is 25-50 MPa; repeating the cycle of homogenization for 3-6 times until the amount of particles below 2 μm is no less than 95% and particles above 5 μm are undetectable; if necessary, using NaOH or HCl to adjust the pH to 4.8 to 8.5, preferably 6.8 to 7.0, most preferably 6.8; and filtering the resulting homogeneous emulsion by nitrogen pressure through a microporous filter of 3 μm or less; filling the emulsion, nitrogenizing, sterilizing and cooling to afford the injection.

The capsule of the invention comprises the following components: *Coix* seed oil 200-800 g, antioxidant(s) and/or emulsifier(s) 0.20-0.60 g for 1000 capsules.

The capsule of the invention can be prepared by a method comprising steps of:

preparing glue solution: weighing gelatin, purified water, glycerin and a preservative at a weight ratio of 1:0.6-1.2:0.3-0.8:0.0001-0.01; adding glycerin, purified water and preservative (selected from any one of 10% ethylparaben solution, benoic acid, potassium sorbate and chlorhexidine acetate) sequentially into a glue melting tank; heating to 70° C.-90; then adding gelatin and constantly stirring the mixture under vacuum until the gelatin is completely dissolved; filtering the glue solution and storing the filtered glue solution at 56-62 for use;

preparing drug liquid: adding formulated amount of *Coix* seed oil, antioxidant (Vitamin E) and/or emulsifier (Tween 80) into an dosing tank, and stirring the mixture constantly until being homogeneously mixed; and pressing capsules: choosing proper pellet dies according to the capsule size; pressing capsules in a tempreture of 15-30 and a relative humidity of less than 35%; drying the pressed and shaped capsules; after removing capsules of abnormal size, washing the normal capsules with 95% medicinal ethanol, and drying them continuously till the moisture content is less than 12%; visually inspecting and removing unqualified capsules; finally printing and packaging to afford the capsules.

It is demonstrated, in pharmacodynamic experiments, that the *Coix* seed oil of the invention and the pharmaceutical preparation thereof have shown different degrees of inhibition on a variety of human tumor cell lines. Thus, the *Coix* seed oil of the invention and pharmaceutical preparations thereof can be used as therapeutical drugs of neoplastic diseases.

Therefore, another aspect of the invention is to provide a method of the treatment of a tumor or an inflammation in a mammal (including human), comprising administering to the mammal (including human) in need a therapeutically effective amount of the *Coix* seed oil of the invention or a pharmaceutical preparation thereof.

The *Coix* seed oil of the invention or the pharmaceutical preparation thereof can be administered alone or in combination with a chemotherapeutic drug selected from one or more of platinums, alkylating agents, difluoro nucleosides, antibiotics, cytotoxics and/or hormons.

Preferably, platinum is selected from cisplatin and carboplatin, the alkylating agent is selected from cyclophosphamide, the difluoro nucleoside is selected from gemcitabine hydrochloride, the antibiotics are selected from mitoxantrone, mitomycin, the cytotoxics are selected from docetaxel, paclitaxel, and the hormone is selected from leuprorelin acetate. Said cancer refers to lung cancer, liver cancer, pancreatic cancer, prostate cancer, ovarian cancer, breast cancer, sarcomatoid carcinoma or cancer sarcoma, in early, middle or late stage; and the inflammation can be prostatic hyperplasia.

The following experimental data are used to illustrate anti-tumor or antiinflammation benefical effects of the *Coix* seed oil of the invention and the pharmaceutical preparations thereof.

I. Inhibition of *Coix* Seed Oil and Preparations Thereof on 8 Human Tumor Cell Lines in MTT Method In Vitro A. Experimental Materials and the Preparation Thereof (1) Cell lines: PANC-1 (human pancreatic cancer cells), SKOV3 (human ovarian cancer cells), MCF-7 (human breast cancer cells), Bcap-37 (human breast cancer cells), SMMC-7721 (human hepatic cancer cells), HepG-2 (human hepatic cancer cells), A549 (human lung cancer cells) and H460 (human lung cancer cells), storaged and passaged maintainably in Research and Evaluation Center for Pharmacology, Shanghai Institute of Pharmaceutical Industry;
(2) DMEM complete medium supplied with 10% newborn calf serum (GIBCO BRL), 1% of penicillin (100 U/mL)+streptomycin (100 μg/mL);
(3) 0.25% trypsin solution, purchased from Invitrogen Corp. and storaged at −20;
(4) Phosphate buffer (PBS): NaCl 8 g, KCl 0.2 g, $Na_2HPO_4$ 1.15 g and $KH_2PO_4$ 0.2 g, dissolved in 1 L double-distilled water and autoclaved at 121 for 20 min, then storaged at 4;
(5) MTT (AMRESCO) solution: 5 mg/ml in PBS;
(6) Formazan crystal dissolving solution: SDS 10 g, isobutanol 5 ml and concentrated hydrochloric acid 0.1 ml, dissolved in 100 ml of deionized double distilled water.

B. Experimental Method

The inhibition effects of samples on the above-mentioned cell lines were detected by using MTT method. The specific procedures were as follows:

(1) Cell culture: (a) Storaged cells were taken out from the liquid nitrogen, thawed quickly in a 37 water bath, then aseptically transferred into 6 ml of cellular medium in a 10 ml centrifugal tube, centrifuged at 1000 rpm for 5 min. The supernatant was discarded, then the precipitated cells were re-suspended in 5-6 ml cellular media by pipetting and transferred into a flask in a 37 incubator for cell culture; (b) Next day, the flask was taken out from the incubator and the used medium was discarded, then the cells were incubated in 5-6 ml fresh medium in the 37 incubator; (c) On the third day, the flask was taken out from the incubator and the used medium was discarded, then 2-3 ml of PBS (pH7.4) was added into the flask with rocking for cleaning it and the used PBS was discarded. Such a cellular cleaning step was repeated once again. 3-5 drops of 0.25% trypsin solution were added into the flask with sloshing, thus well-distributed in it. The flask was capped and placed in a 37 incubator for about 3 min, and the separation of cells from the flask wall was observed under the microscope. 2 ml of cellular medium was added and cells were separated completely from the flask wall by pipetting, then the cell suspension was transferred into 2 separate clean flasks, each containing 5-6 ml medium. The cell suspension was well-distributed by pipetting, then the flask was placed in a 37 incubator. (d) Step (c) was repeated every other day. In the whole cultivation process, adherent cells were not allowed to grow too dense and suspension cells were always maintained at a logarithmic growth stage.

(2) Preparation of the sample and the control: A proper amount of sample of *Coix* seed oil (oil of Job's tears seed) was dissolved in DMSO to obtain a solution in a concentration of 10 mg/ml. This solution was diluted in a gradient dilution with PBS to obtain a set of sample solutions in the concentration of 10 mg/ml, 5000 μg/ml, 2500 μg/ml, 1250 μg/ml, 625 μg/ml and 312.5 μg/ml, respectively.

(3) Each diluted sample solution was added into duplicated wells of a 96 well flat-bottom microplate (10 μl/well). The correspondingly diluted DMSO solutions, as controls, were added into the wells of the microplate.

(4) Cells in a logarithmic growth stage were trypsinized and washed, then re-suspended in the medium containing 10% calf serum. The number of living cells was counted in Trypan blue dye exclusion method and cell suspensions were adjusted into a density of $2 \times 10^5$ cell/ml.

(5) The cell-contained 96 well flat-bottom microplate was placed in a 37 incubator and cells were incubated under 5% $CO_2$ for 48 h.

(6) 20 μl of 5 mg/ml MTT solution was added into each well and cells were incubated continuously in the incubator for 3-4 h.

(7) 100 μl of crystal dissolving solution was added into each well and cells were incubated continuously in the incubator overnight, so as to dissolve the resulted formazan crystals sufficiently. Then, the absorbance value was measured at 570 nm for each well.

(8) Based on absorbance values, inhibition rates on the cell growth were calculated for sample groups of various concentrations. The calculation formula was as follows:

(1−mean absorbance of experimental wells/mean absorbance of control wells)×100%

C. Experimental Results

TABLE 1

Inhibition rates of samples in various concentrations on the cell growth in 8 cell lines (%)

| Cell line | Concentration of Sample | | | | | |
|---|---|---|---|---|---|---|
| | 1000 μg/ml | 500 μg/ml | 250 μg/ml | 125 μg/ml | 62.5 μg/ml | 31.25 μg/ml |
| PANC-1 | 98.77 | 73.83 | 26.24 | 18.93 | 15.96 | 2.95 |
| SKOV3 | 98.85 | 59.52 | 26.70 | 16.43 | 3.43 | 1.31 |
| MCF-7 | 98.47 | 65.68 | 23.29 | 11.85 | 7.02 | 0.42 |
| Bcap-37 | 99.63 | 73.03 | 36.34 | 17.34 | 2.29 | 1.40 |
| SMMC-7721 | 98.54 | 70.73 | 39.44 | 22.37 | 14.70 | 3.12 |
| HepG-2 | 98.47 | 65.35 | 38.30 | 26.22 | 16.02 | 1.07 |
| A549 | 99.02 | 74.97 | 56.85 | 42.61 | 22.00 | 1.48 |
| H460 | 97.16 | 73.47 | 56.36 | 44.13 | 18.45 | 7.14 |

TABLE 2

$IC_{50}$ values of samples in 8 cell lines in vitro (μg/ml)

| | Sample | |
|---|---|---|
| Cell line | Coix seed oil | Positive control (Taxol) |
| PANC-1 | 213.1 | 0.44 |
| SKOV3 | 262.8 | 0.22 |
| MCF-7 | 275.5 | 0.18 |
| Bcap-37 | 220.7 | 0.28 |
| SMMC-7721 | 205.9 | 0.41 |
| HepG-2 | 222.5 | 0.45 |
| A549 | 173.2 | 0.46 |
| H460 | 166.9 | 0.49 |

D. Conclusion

The *Coix* seed oil of the invention in various concentrations has shown the inhibition on 8 human tumor cell lines in different degrees.

2. Inhibition Rate of the Injection of the Invention on the Growth of A549 Human Lung Cancer Transplanted in Nude Mice A. Experimental Materials The injection of the invention (10 g/100 ml), Cisplatin (Qilu Phamaceutical Co., Ltd), blank fat emulsion and normal saline

B. Experimental Method

A549 Human lung cancer cells cryopreserved in liquid nitrogen were recovered, and incubated in a 37 incubator under 5% $CO_2$. After being subcultured, cells in a logarithmic growth stage were distributed with normal saline to be a cell suspension in a concentration of $1-2\times10^7$ cells/ml. The cell suspension was inoculated into BALB/C nude mice (SPF grade, 18-20 g, 6 weeks old, male) subcutaneously at right axillary. The tumor tissues were aseptically taken from the $2^{nd}$ generation of xenograft model of A549 human lung cancer in a vigorous growth stage and cut into small uniform pieces in the size of 1-2 $mm^3$. The right axillary of each nude mouse was inoculated one piece subcutaneously via a trocar. When the inoculated tumor could be touched, the mice were randomly grouped and administered according to the experimental design program. All contacted feed, padding, cages and equipment, etc., should be autoclaved prior to use. The nude mice were fed in a laminar flow rack. Tumor sizes and animal weights were observed and tested dynamically. Mice in each group were sacrificed 3 weeks later or so, and tumors were surgically removed and weighed. The inhibition rate on tumor was calculated according to the following formula:

Inhibition rate %=[(Mean tumor weight of the control group−mean tumor weight of the treatment group)/mean tumor weight of the control group]×100%;

Q value of antitumor effect in drug combination was calculated according to Jin's formula:

$$Q=E_{a+b}/(E_a+E_b-E_a\times E_b)$$

Wherein $E_{a+b}$=the tumor inhibition rate of drug combination, $E_a$ or $E_b$=the tumor inhibition rate of drug A or drug B, respectively. If Q value=0.85-1.15, an additive effect (+) was shown; if Q value>1.15, a synergistic effect (++) was shown.

C. Experimental Results

D. Experimental Conclusion

It is shown that the injection of the invention (25 ml/kg, 12.5 ml/kg and 6.25 ml/kg, iv×10 qd) has a significant tumor inhibition effect on the growth of A549 human lung cancer transplanted in nude mice.

It is shown that the tumor inhibition effect of the co-administration of the injection of the invention with cisplatin was significantly stronger than that of the injection of the invention or that of cisplatin, alone, on A549 human lung cancer transplanted in nude mice, i.e., the co-administration has shown a significant additive effect.

3. The Tumor Inhibition Rate of the Injection of the Invention on the Growth of QGY Human Hepatoma Transplanted in Nude Mice

A. Experimental Materials

The injection of the invention (10 g/100 ml), Adriamycin (Pfizer Italia S.r.1), blank fat emulsion and normal saline

B. Experimental Method

QGY human hepatoma cells cryopreserved in liquid nitrogen were recovered, and incubated in a 37 incubator under 5% $CO_2$. Other steps were the same as mentioned in 2-B.

TABLE 3

Efficacy of anti-tumor on Xenograft model of A549 human lung cancer inoculated subcutaneously in nude mice

| Sample group | Dosage | Dosage regimen | Number of animal start/end | Weight of animal (g) start/end | Weight of tumor (g) $\bar{x} \pm SD$ | Inhibition Rate % | Q |
|---|---|---|---|---|---|---|---|
| The injection | 25 ml/kg | iv × 10 qd | 6/6 | 20.2/24.3 | 0.623 ± 0.19** | 52.87 | |
| The injection | 12.5 ml/kg | iv × 10 qd | 6/6 | 20.1/25.2 | 0.788 ± 0.19** | 40.39 | |
| The injection | 6.25 ml/kg | iv × 10 qd | 6/6 | 20.6/25.3 | 0.845 ± 0.15** | 36.08 | |
| The injection + Cisplatin | (25 ml + 1 mg)/kg | iv × 10 qd + ip × 7 qd | 6/6 | 20.1/25.3 | 0.458 ± 0.10** | 65.36 | 0.8987 |
| The injection + Cisplatin | (12.5 ml + 1 mg)/kg | iv × 10 qd + ip × 7 qd | 6/6 | 20.2/24.5 | 0.501 ± 0.11** | 62.10 | 0.9480 |
| The injection + Cisplatin | (6.25 ml + 1 mg)/kg | iv × 10 qd + ip × 7 qd | 6/6 | 20.1/25.4 | 0.558 ± 0.11** | 57.79 | 0.9172 |
| Cisplatin | 1 mg/kg | ip × 7 qd | 6/6 | 20.2/24.0 | 0.765 ± 0.11** | 42.13 | |
| Cisplatin | 2 mg/kg | ip × 7 qd | 6/6 | 20.4/23.1 | 0.181 ± 0.06** | 86.31 | |
| Blank fat emulsion | 25 ml/kg | iv × 10 qd | 6/6 | 20.1/26.5 | 1.325 ± 0.34 | — | |
| Control (NS) | 25 ml/kg | iv × 10 qd | 6/6 | 20.3/26.6 | 1.322 ± 0.32 | — | |

*$P < 0.05$,
**$P < 0.01$, compared with NS negative control group.

C. Experimental Results

TABLE 4

Efficacy of anti-tumor on Xenograft model of QGY human hepatoma inoculated subcutaneously in nude mice

| Sample group | Dosage | Dosage regimen | Number of animal start/end | Weight of animal (g) start/end | Weight of tumor (g) $\bar{x} \pm SD$ | Inhibition rate % | Q |
|---|---|---|---|---|---|---|---|
| The injection | 25 ml/kg | iv × 10 qd | 6/6 | 21.4/25.6 | 0.680 ± 0.18** | 41.18 | |
| The injection | 12.5 ml/kg | iv × 10 qd | 6/6 | 21.4/25.2 | 0.787 ± 0.15** | 31.92 | |
| The injection | 6.25 ml/kg | iv × 10 qd | 6/6 | 21.5/24.9 | 0.790 ± 0.18* | 31.66 | |
| The injection + Adriamycin | (25 ml + 1 mg)/kg | Iv × 10 qd + ip × 7 qd | 6/6 | 21.8/24.9 | 0.502 ± 0.16** | 56.57 | 0.8870 |
| The injection + Adriamycin | (12.5 ml + 1 mg)/kg | iv × 10 qd + ip × 7 qd | 6/6 | 21.5/24.7 | 0.598 ± 0.15** | 48.27 | 0.8312 |
| The injection + Adriamycin | (6.25 ml + 1 mg)/kg | iv × 10 qd + ip × 7 qd | 6/6 | 21.8/24.7 | 0.627 ± 0.12** | 45.76 | 0.7902 |
| Adriamycin | 1 mg/kg | ip × 7 qd | 6/6 | 21.3/24.6 | 0.712 ± 0.18** | 38.41 | |
| Adriamycin | 2 mg/kg | ip × 7 qd | 6/6 | 21.8/23.1 | 0.338 ± 0.17** | 70.76 | |
| Blank fat mulsion | 25 ml/kg | iv × 10 qd | 6/6 | 21.6/26.9 | 1.125 ± 0.15 | — | |
| NS | 25 ml/kg | iv × 10 qd | 6/6 | 21.5/26.7 | 1.156 ± 0.24 | — | |

*$P < 0.05$,
**$P < 0.01$, compared with negative control group (NS).

D. Experimental Conclusion

It is shown that the injection of the invention (25 ml/kg, 12.5 ml/kg and 6.25 ml/kg, iv×10 qd) has a significant tumor inhibition effect on the growth of QGY human hepatoma transplanted in nude mice.

It is shown that the tumor inhibition effect of the co-administration of the injection of the invention with Adriamycin was significantly stronger than that of the injection of the invention or Adriamycin, alone, on QGY human hepatoma transplanted in nude mice.

4. The Tumor Inhibition Rate of the Injection of the Invention on LM-3 Human Hepatoma Transplanted in Nude Mice A. Experimental Materials The injection of the invention (10 g/100 ml), cyclophosphamide (Jiangsu Hengrui Medicine Co., Ltd), blank fat emulsion and normal saline B. Experimental Method LM-3 human hepatoma cells cryopreserved in liquid nitrogen were recovered, and incubated in a 37 incubator under 5% $CO_2$. Other steps were the same as mentioned in 2-B.

C. Experimental Results

TABLE 5

Efficacy of anti-tumor on Xenograft model of LM-3 human hepatoma inoculated subcutaneously in nude mice

| Sample group | Dosage | Dosage regimen | Number of animal start/end | Weight of animal (g) start/end | Weight of tumor (g) $\bar{x} \pm SD$ | Inhibition rate % | Q |
|---|---|---|---|---|---|---|---|
| The injection | 25 ml/kg | iv × 10 qd | 6/6 | 20.2/26.3 | 1.043 ± 0.16** | 32.05 | |
| The injection | 12.5 ml/kg | iv × 10 qd | 6/6 | 20.3/26.2 | 1.092 ± 0.28** | 28.86 | |
| The injection | 6.25 ml/kg | iv × 10 qd | 6/6 | 20.4/27.0 | 1.251 ± 0.27** | 18.50 | |
| The injection + cyclophosphamide | (25 ml + 15 mg)/kg | iv × 10 qd + ip × 7 qd | 6/6 | 20.4/26.6 | 0.755 ± 0.13** | 50.81 | 0.9972 |
| The injection + cyclophosphamide | (12.5 ml + 15 mg)/kg | iv × 10 qd + ip × 7 qd | 6/6 | 20.3/28.1 | 0.778 ± 0.17** | 49.32 | 1.0137 |
| The injection + cyclophosphamide | (6.25 ml + 15 mg)/kg | iv × 10 qd + ip × 7 qd | 6/6 | 20.4/25.8 | 0.862 ± 0.19** | 43.84 | 1.0648 |
| cyclophosphamide | 15 mg/kg | ip × 7 qd | 6/6 | 20.7/24.8 | 1.108 ± 0.09** | 27.82 | |
| cyclophosphamide | 30 mg/kg | ip × 7 qd | 6/6 | 20.5/25.0 | 0.265 ± 0.12** | 82.74 | |
| Blank fat emulsion | 25 ml/kg | iv × 10 qd | 6/6 | 20.4/27.8 | 1.557 ± 0.30 | — | |
| NS | 25 ml/kg | iv × 10 qd | 6/6 | 20.6/28.0 | 1.535 ± 0.28 | — | |

*$P < 0.05$,
**$P < 0.01$, compared with negative control group (NS).

D. Experimental Conclusion

It is shown that the injection of the invention (25 ml/kg, 12.5 ml/kg and 6.25 ml/kg, iv×10 qd) has a significant tumor inhibition effect on the growth of LM-3 human hepatoma transplanted in nude mice.

It is shown that the tumor inhibition effect of the co-administration of the injection of the invention with cyclophosphamide was significantly stronger than that of the injection of the invention or cyclophosphamide, alone, on LM-3 human hepatoma transplanted in nude mice, i.e., the co-administration has shown a significant additive effect.

5. The Tumor Inhibition Rate of the Injection of the Invention on the Growth of SMMC-7721 Human Hepatoma Transplanted in Nude Mice

A. Experimental Materials

The injection of the invention (10 g/100 ml), gemcitabine hydrochloride (LILLY FRANCE), blank fat emulsion and normal saline

B. Experimental Method

SMMC-7721 human hepatoma cells cryopreserved in liquid nitrogen were recovered, and incubated in a 37 incubator under 5% $CO_2$. Other steps were the same as mentioned in 2-B.

C. Experimental Results

D. Experimental Conclusion

It is shown that the injection of the invention (25 ml/kg, 12.5 ml/kg and 6.25 ml/kg, iv×10 qd) has a significant tumor inhibition effect on the growth of SMMC-7721 human hepatoma transplanted in nude mice.

It is shown that the tumor inhibition effect of the co-administration of the injection of the invention with gemcitabine hydrochloride was significantly stronger than that of the injection of the invention or gemcitabine hydrochloride, alone, on SMMC-7721 human hepatoma transplanted in nude mice, i.e., the co-administration has shown a significant additive effect.

6. The Inhibition Rate of the Injection of the Invention on S180 Sarcoma Transplanted in Mice

A. Experimental Materials

The injection of the invention (10 g/100 ml), Cyclophosphamide (CTX), Mitoxantrone (DHAD), Mitomycin (MMC) and normal saline S180 sarcoma: inoculated in Kunmin mice, 19-21 g, female

B. Experimental Method

Ascitic fluid of mice having well-grown S180 sarcoma was diluted with normal saline (1:4) to obtain a cell suspension of about $1-2\times10^7$ cells/ml. Each mouse was inoculated with 0.2 ml of the suspension subcutaneously at the right axilla, and the mice were grouped randomly. The administration began from the next day according to the dosage program in Table 7. On the tenth day after the inoculation of S180, animals were sacrificed via cervical dislocation and dissected to take out the tumor block. Weights of tumor were compared and inhibition rates were calculated for each group.

TABLE 6

Efficacy of anti-tumor on Xenograft model of SMMC-7721 human hepatoma inoculated subcutaneously in nude mice

| Sample group | Dosage | Dosage regimen | Number of animal start/end | Weight of animal (g) start/end | Weight of tumor (g) $\bar{x} \pm SD$ | Inhibition rate % | Q |
|---|---|---|---|---|---|---|---|
| The injection | 25 ml/kg | iv × 10 qd | 6/6 | 20.4/25.1 | 0.876 ± 0.13** | 49.71 | |
| The injection | 12.5 ml/kg | iv × 10 qd | 6/6 | 20.4/25.6 | 0.942 ± 0.21** | 45.92 | |
| The injection | 6.25 ml/kg | iv × 10 qd | 6/6 | 20.1/24.8 | 1.041 ± 0.23** | 40.24 | |
| The injection + Gemcitabine | (25 ml + 25 mg)/kg | iv × 10 qd + iv × 3 q 3 d | 6/6 | 20.5/26.1 | 0.610 ± 0.09** | 64.98 | 0.8731 |
| The injection + Gemcitabine | (12.5 ml + 25 mg)/kg | iv × 10 qd + iv × 3 q 3 d | 6/6 | 20.9/26.5 | 0.632 ± 0.14** | 63.72 | 0.8790 |
| The injection + Gemcitabine | (6.25 ml + 25 mg)/kg | iv × 10 qd + iv × 3 q 3 d | 6/6 | 20.4/26.4 | 0.661 ± 0.16** | 62.06 | 0.8916 |
| Gemcitabine | 25 mg/kg | iv × 3 q 3 d | 6/6 | 20.1/25.1 | 0.886 ± 0.24** | 49.14 | |
| Gemcitabine | 50 mg/kg | iv × 3 q 3 d | 6/6 | 20.4/24.2 | 0.215 ± 0.11** | 87.66 | |
| Blank fat emulsion | 25 ml/kg | Iv × 10 qd | 6/6 | 20.2/26.1 | 1.765 ± 0.19 | | |
| NS | 25 ml/kg | iv × 10 qd | 6/6 | 20.8/26.9 | 1.742 ± 0.24 | | |

*$P < 0.05$,
**$P < 0.01$, compared with negative control group (NS).

C. Experimental Results

TABLE 7

Efficacy of anti-tumor on S180 sarcoma model in mice

| Sample group | Dosage | Dosage regimen | Number of animal start/end | Weight of tumor (g) $\bar{x} \pm SD$ | Inhibition rate % | Q |
|---|---|---|---|---|---|---|
| The injection | 25 ml/kg | iv × 7 | 10/10 | 1.18 ± 0.23 | 25.32* | |
| The injection + CTX | 25 ml/kg + 30 mg/kg | iv × 7 + ip × 2(1, 3) | 10/10 | 0.79 ± 0.14 | 50.00** | 0.8847 |
| CTX | 30 mg/kg | Ip × 2(1, 3) | 10/10 | 0.92 ± 0.21 | 41.77* | |
| The injection + DHAD | 25 ml/kg + 2 mg/kg | iv × 7 + ip × 2(1, 3) | 10/10 | 0.52 ± 0.13 | 67.09** | 1.0627 |
| DHAD | 2 mg/kg | Ip × 2(1, 3) | 10/10 | 0.78 ± 0.20 | 50.63** | |
| The injection + MMC | 25 ml/kg + 1.5 mg/kg | iv × 7 + ip × 2(1, 3) | 10/10 | 0.62 ± 0.12 | 60.76** | 1.1220 |
| MMC | 1.5 mg/kg | Ip × 2(1, 3) | 10/10 | 0.97 ± 0.19 | 38.61* | |
| Control (NS) | 25 ml/kg | iv × 7 | 10/10 | 1.58 ± 0.36 | — | |

*$P < 0.05$,
**$P < 0.01$, compared with negative control group (NS).

D. Experimental Conclusion

It is shown in the results that the injection of the invention in combination with CTX, DHAD or MMC has a tumor inhibition effect that is significantly stronger than that of the injection of the invention or chemotherapy drug alone, i.e., the co-administration has shown a significant additive effect.

7. The Inhibition Rate of the Injection of the Invention on W256 Cancer Sarcoma Transplanted in Rats

A. Experimental Materials

The injection of the invention (10 g/100 ml), Cyclophosphamide (CTX) and normal saline W256 cancer sarcoma: inoculated in Wistar rats, 50-60 g, female

B. Experimental Method

Ascitic fluid of rats with well-grown W256 cancer sarcoma was diluted with normal saline to obtain a cell suspension of about $1-2 \times 10^7$ cells/ml. Each rat was inoculated with 0.2 ml of the suspension at the right axilla subcutaneously. The rats were grouped randomly next day and began administration. Two weeks later, animals were sacrificed and dissected to take out the tumor block. Weights of tumor were compared between each experimental group and the control group and tumor inhibition rates were calculated.

C. Experimental Results

TABLE 8

Efficacy of anti-tumor on the model of W256 cancer sarcoma in rats

| Sample group | Dosage | Dosage regimen | Number of animal start/end | Weight of tumor (g) $\bar{x} \pm SD$ | Inhibition rate % | Q |
|---|---|---|---|---|---|---|
| CTX | 30 mg/kg | iv × 7 | 10/8 | 0.42 ± 0.85 | 87.68** | |
| CTX | 10 mg/kg | iv × 2(3, 5) | 10/10 | 2.12 ± 1.22 | 37.83* | |
| The injection | 20 ml/kg | iv × 10 | 10/10 | 1.44 ± 0.72 | 57.78** | |
| The injection + CTX | 20 ml/kg + 10 mg/kg | iv × 10 + iv × 2(3, 5) | 10/10 | 0.94 ± 0.32 | 72.43** | 0.9821 |
| The injection | 10 ml/kg | iv × 10 | 10/10 | 1.88 ± 0.71 | 44.87** | |
| The injection + CTX | 10 ml/kg + 10 mg/kg | iv × 10 + iv × 2(3, 5) | 10/10 | 1.02 ± 0.58 | 70.09** | 1.0664 |
| The injection | 5 ml/kg | iv × 10 | 10/9 | 2.13 ± 1.19 | 37.54* | |
| The injection + CTX | 5 ml/kg + 10 mg/kg | iv × 10 + iv × 2(3, 5) | 10/10 | 1.68 ± 0.98 | 50.73** | 0.8293 |
| Control (NS) | 20 ml/kg | iv × 10 | 10/10 | 3.41 ± 1.16 | — | |

*$P < 0.05$,
**$P < 0.01$, compared with negative control group (NS).

D. Experimental Conclusion

It is shown in the results that the injection of the invention in combination with CTX has a tumor inhibition effect that is significantly stronger than that of the injection of the invention or the chemotherapy drug alone, i.e., the co-administration has shown a significant additive effect.

8. The Tumor Inhibition Rate of the Injection of the Invention on PANC-1 Human Pancreatic Cancer Transplanted in Nude Mice

A. Experimental Materials

The injection of the invention (10 g/100 ml), Gemcitabine hydrochloride and normal saline PANC-1 human pancreatic cancer cells: inoculated in BALB/C nude mice, 16-18 g, female

B. Experimental Method

Tumor blocks of well-grown PANC-1 human pancreatic cancer were inoculated subcutaneously in 4-week-old female BALB/C nude mice. The nude mice were grouped randomly and administered. One week after the end of the administration, the mice were sacrificed and dissected. Tumor blocks were taken out and weighed. Differences of tumor weight between each experimental group and the control group were compared and the tumor inhibition rates were calculated.

C. Experimental Results

TABLE 9

Efficacy of anti-tumor on model of PANC-1 human pancreatic cancer in nude mice

| Sample group | Dosage | Dosage regimen | Number of animal start/end | Weight of tumor (g) $\bar{x} \pm SD$ | Inhibition rate % | Q |
|---|---|---|---|---|---|---|
| Gemcitabine | 60 mg/kg | iv × 1 | 6/6 | 0.1443 ± 0.081 | 24.61 | |
| The injection | 50 ml/kg | iv × 10 | 6/6 | 0.1491 ± 0.013 | 22.10 | |
| The injection + Gemcitabine | 50 ml/kg + 60 mg/kg | iv × 10 + iv × 1 | 6/6 | 0.0921 ± 0.043 | 51.88 | 1.2570 |
| Control (NS) | 50 ml/kg | iv × 10 | 6/6 | 0.1914 ± 0.087 | — | |

It is shown in the results that the injection of the invention in combination with gemcitabine hydrochloride has a tumor inhibition effect that is significantly stronger than that of the injection of the invention or the chemotherapy drug alone, i.e., the co-administration has shown a significant additive effect.

9. The Tumor Inhibition Rate of the Injection of the Invention on FC-3M Human Prostate Cancer Transplanted in Nude Mice

A. Experimental Materials

The injection of the invention (10 g/100 ml), Leuprolide acetate (Lupron) and normal saline
FC-3M human prostate cancer: inoculated in BALB/C nude mice, 17-21 g, male

B. Experimental Method

Tumor blocks of well-grown FC-3M human prostate cancer were homogenized in normal saline (1:4). Each nude mouse was inoculated with 0.2 ml of the suspension at the right axilla subcutaneously, and the mice were grouped randomly. The administration began from the next day. 21 Days after the inoculation, the mice were sacrificed. Tumor blocks were taken out and weighed. Differences of tumor weight between each experimental group and the control group were compared and the tumor inhibition rates were calculated.

C. Experimental Results

TABLE 10

Efficacy of anti-tumor on model of FC-3M human prostate cancer in nude mice

| Sample group | Dosage | Dosage regimen | Number of animal start/end | Weight of tumor (g) $\bar{x} \pm SD$ | Inhibition rate % | Q |
|---|---|---|---|---|---|---|
| Lupron | 0.75 ml/kg | iv × 1 | 6/6 | 0.98 ± 0.23 | 36.36** | |
| Lupron | 1.5 ml/kg | iv × 1 | 6/6 | 0.76 ± 0.14 | 50.65** | |
| The injection | 12.5 ml/kg | iv × 10 | 6/6 | 1.12 ± 0.24 | 27.27 | |
| The injection + Lupron | 12.5 ml/kg + 0.75 ml/kg | iv × 10 + iv × 1 | 6/6 | 0.52 ± 0.13 | 66.23** | 1.2330 |
| The injection | 25 ml/kg | iv × 10 | 6/6 | 0.77 ± 0.15 | 50.00** | |
| The injection + Lupron | 25 ml/kg + 1.5 ml/kg | iv × 10 + iv × 1 | 6/6 | 0.45 ± 0.16 | 70.78** | 0.9397 |
| Control (NS) | 25 ml/kg | iv × 10 | 6/6 | 1.54 ± 0.20 | — | |

*$P < 0.05$,
**$P < 0.01$, compared with the control group.

It is shown in the results that the injection of the invention in combination with Lupron has a tumor inhibition effect that is significantly stronger than that of the injection of the invention or the chemotherapy drug alone, i.e., the co-administration has shown a significant additive effect.

10. The Tumor Inhibition Rate of the Injection of the Invention on Bcap37 Human Breast Cancer Transplanted in Nude Mice

A. Experimental Materials

The injection of the invention (10 g/100 ml), Docetaxel injection (Taxotere, 20 mg/vial) and normal saline Bcap-37 human breast cancer: inoculated in BALB/C nude mice (SPF grade), 18-20 g, female

B. Experimental Method

Tumor blocks of well-grown Bcap-37 human breast cancer were homogenized in normal saline to obtain cell suspensions in the concentration of $1$-$2\times10^7$ cells/ml. Each nude mouse was inoculated with 0.2 ml of the suspension at the right axilla subcutaneously, and the mice were grouped randomly. The administration began from the 7th day after the inoculation. 20 Days after the inoculation, the mice were sacrificed. Tumor blocks were taken out and weighed. Differences of tumor weight between each experimental group and the control group were compared, and tumor inhibition rates and Q values were calculated.

C. Experimental Results

TABLE 11

Efficacy of anti-tumor on model of Bcap-37 human breast cancer in nude mice

| Sample group | Dosage | Dosage regimen | Number of animal start/end | Weight of tumor (g) $\bar{x} \pm SD$ | Inhibition rate % | Q |
|---|---|---|---|---|---|---|
| Control (NS) | 25 ml/kg | iv × 10 | 10/10 | 2.94 ± 0.81 | | |
| Docetaxel | 25 mg/kg | ip × 1 | 6/6 | 1.27 ± 0.88** | 56.80 | |
| The injection | 6.25 ml/kg | iv × 10 | 6/6 | 1.86 ± 0.32** | 36.73 | |
| | 12.5 ml/kg | iv × 10 | 6/6 | 1.41 ± 0.65** | 52.04 | |
| | 25 ml/kg | iv × 10 | 6/6 | 1.18 ± 0.59** | 59.86 | |
| The injection + Docetaxel | 6.25 ml/kg + 25 mg/kg | iv × 10 + ip × 1 | 6/6 | 0.87 ± 0.45** | 70.41 | 0.9689 |
| The injection + Docetaxel | 12.5 ml/kg + 25 mg/kg | iv × 10 + ip × 1 | 6/6 | 0.94 ± 0.98** | 68.03 | 0.8581 |
| The injection + Docetaxel | 25 ml/kg + 25 mg/kg | iv × 10 + ip × 1 | 6/6 | 0.72 ± 0.36** | 75.51 | 0.9135 |

*$P < 0.05$,
**$P < 0.01$, compared with the negative control group.

The tumor inhibition effects of the injection of the invention in combination with Docetaxel injection were significantly stronger than that of the injection of the invention or Docetaxel, alone, on Bcap-37 human breast cancer transplanted in nude mice. It has been demonstrated in this experiment that the combination of the injection of the invention with Docetaxel has shown a significant additive effect.

11. The Tumor Inhibition Rate of the Injection of the Invention on MDA-MB-435 Human Breast Cancer Transplanted in Nude Mice

A. Experimental Materials

The injection of the invention (10 g/100 ml), Paclitaxel injection (30 mg/5 ml) and normal saline MDA-MB-435 human breast cancer: inoculated in BALB/C nude mice (SPF grade), 18-20 g, female

B. Experimental Method

Tumor blocks of well-grown MDA-MB-435 cancer were homogenized in normal saline to obtain cell suspensions in the concentration of $1$-$2\times10^7$ cells/ml. Each nude mouse was inoculated with 0.2 ml of the suspension at the right axilla subcutaneously, and the mice were grouped randomly. The administration began from the 7th day after the inoculation. 18 Days after the inoculation, the mice were sacrificed. Tumor blocks were taken out and weighed. Differences of tumor weight between each experimental group and the control group were compared, and tumor inhibition rates and Q values were calculated.

C. Experimental Results

TABLE 12

Efficacy of anti-tumor on the model of MDA-MB-435 human breast cancer in nude mice

| Sample | Dosage | Dosage regimen | Number of animal start/end | Weight of tumor (g) $\bar{x} \pm SD$ | Inhibition rate % | Q |
|---|---|---|---|---|---|---|
| Control (NS) | 25 ml/kg | iv × 10 | 12/12 | 2.72 ± 0.39 | | |
| Paclitaxel | 50 mg/kg | ip × 1 | 6/6 | 1.01 ± 0.33** | 62.87 | |
| The injection | 6.25 ml/kg | iv × 10 | 6/6 | 1.53 ± 0.26** | 43.75 | |
| | 12.5 ml/kg | iv × 10 | 6/6 | 1.22 ± 0.25** | 55.15 | |
| | 25 ml/kg | iv × 10 | 6/6 | 0.66 ± 0.07** | 75.74 | |
| The injection + Paclitaxel | 6.25 ml/kg + 50 mg/kg | iv × 10 + ip × 1 | 6/6 | 0.93 ± 0.48** | 65.81 | 0.8318 |
| The injection + Paclitaxel | 12.5 ml/kg + 50 mg/kg | iv × 10 + ip × 1 | 6/6 | 0.76 ± 0.45** | 72.06 | 0.8646 |

TABLE 12-continued

Efficacy of anti-tumor on the model of MDA-MB-435 human breast cancer in nude mice

| Sample | Dosage | Dosage regimen | Number of animal start/end | Weight of tumor (g) $\bar{x} \pm SD$ | Inhibition rate % | Q |
|---|---|---|---|---|---|---|
| The injection + Paclitaxel | 25 ml/kg + 50 mg/kg | iv × 10 + ip × 1 | 6/6 | 0.48 ± 0.32** | 82.35 | 0.9050 |

*P < 0.05,
**P < 0.01, compared with the negative control group.

The tumor inhibition effects of the injection of the invention in combination with Paclitaxel injection were significantly stronger than that of the injection of the invention or Paclitaxel injection, alone, on MDA-MB-435 human breast cancer transplanted in nude mice. It has been demonstrated in this experiment that the combination of the injection of the invention with Paclitaxel injection has shown a significant additive effect.

12. The Clinical Efficacy of the Capsules of the Invention in Combination with Chemotherapy in the Treatment of Ovarian Cancer A. Clinical Data and Treatment Method 58 patients suffering from late stage ovarian cancer were randomly divided into two groups: Group I, capsule of the invention and Group II, control. 30 Cases in Group I were treated with TC program (Taxol+Carboplatin) in combination with the capsule of the invention; and 28 cases of the control group were treated with TC program merely. The baseline data of both groups were balanced (p>0.05). Taxol (175 mg/m²) was administered on day 1 and Carboplatin AUC=5 was administered on day 1 and repeated every 3 weeks. 4-6 Cycles of chemotherapy was performed based on patient's benefit situation. The capsule of the invention (6 capsules, t.i.d.) was administered continuously until the occurrence of disease progression or intolerable toxic and side effects.

B. Therapeutic Evaluation (1) Response rate and disease control rate: Short-term effects were evaluated and analyzed every 2 cycles of chemotherapy using RECIST criteria, and the results of evaluation were divided into 4 grades: complete response (CR), partial response (PR), stable disease (SD) and progression of disease (PD). Response rate (RR) was calculated by using CR+PR; and disease control rate (DCR) was calculated by using CR+PR+SD. Therapeutical effects were confirmed for all CR and PR patients four weeks later.

(2) Toxic and side effects: Common Terminology Criteria (NCI-CTC AE) version 3.0 was used to analyze adverse effects. Toxic reactions were scored as 0-V grades.

C. Results (1) Short-term effects: Group I, the response rate was 46.7% (0 case in CR grade, 14 cases in PR grade, 8 cases in SD grade and 8 cases in PD grade), and the disease control rate was 73.3%; Group II, the response rate was 39.3% (0 case in CR grade, 11 cases in PR grade, 6 cases in SD grade and 11 cases in PD grade), and the disease control rate was 60.7%. Both the response rate and the disease control rate in Group I were significantly higher than those in Group II.

(2) Toxic and side effects: It has been shown in the evaluation for 58 patients that the most common toxic and side effects were gastrointestinal reactions, myelosuppression, neurotoxicity, myalgia and arthralgia, etc. The incidences of grade ¾ myelosuppression in the group of the invention (Group I) and the control group (Group II) were 42.5% and 54%, respectively; the incidences of grade ¾ febrile neutropenia/infection in the group of the invention (Group I) and the control group (Group II) were 12% and 19%, respectively. There was no death case in both groups. Nausea, vomiting, neurotoxicity, myalgia and arthralgia were more common in the control group. The incidence of fatigue in the group of the invention was significantly lower than that in the control group.

Thus it can be seen that the combination of the capsule of the invention with Taxol+Carboplatin has a higher response rate in the treatment of late stage ovarian cancer and a lower chemotherapy-related toxic reaction, and can effectively improve the patients' life quality.

13. The Effect of the Capsule of the Invention on Prostate Hyperplasia Induced by the Implantation of Urogenital Sinus in Mice A. Experimental Materials The capsule of the invention, Prostate Tablet (Cerniton®, PuShiTaiPian) (pollen extracts P5 70 mg, EA10 4 mg), NaCl injection (2.25 g/250 ml; 250 ml/bottle), Pentobarbital sodium, olive oil, penicillin sodium for injection (800,000 units/vial)

Animal: ICR mice, clean grade, fasting overnight prior to use.

B. Experimental Method

Preparation of urogenital sinus: ICR mice in sexual maturity, twenty female and ten male, 25-30 g, were caged in the ratio of female:male=2:1. Every morning, the vulva of each mouse was expanded by using a pincet to inspect whether a vaginal plug appeared. The phenomenon of the appearance of a white emboli pluged in the vagina, which was formed by the solidified semen, indicates that the copulation had occurred. The day when vaginal plug appeared was considered as day 1 of pregnancy. The female mouse, at the 16th days after fertilization, was sacrificed and the 16 day-old embryo was aseptically taken out. The urogenital sinus was placed into a glass petri dish filled with normal saline and reserved.

Modeling: Sixty male ICR mice (25-30 g) in sexual maturity were anesthetized with pentobarbital sodium via intraperitoneal injection. The abdoman of each mouse was aseptically incised and the ventral prostate was separated carefully. Urogenital sinus tissues from three 16 days-old fetus of the same strain mice were transplanted into the ventral prostate. 10 mice in the sham operation group were merely punctured in abdomen but not implanted with urogenital sinus tissues. All mice were given penicillin (20,000 units, i.p.) for three days after the operation.

Grouping and administering: The mice without abnormalities, three days after the operation, were divided into the following groups: sham operation group, model group, positive control group (Cernilton 60 mg/kg), and groups of the capsule of the invention (high-dose 9 g/kg, middle-dose 3 g/kg and low-dose 1 g/kg). The intragastric administration (0.1 ml/10 g) was performed for 28 days, and the mice in the sham operation group and the model group were merely given with the same volume of olive oil.

Detection indexes: (1) body weight, (2) wet weight of ventral prostate and prostate index (wet weight of prostate/body weight), (3) pathological changes of ventral prostate tissues (Scoring criteria is shown in Table 13).

TABLE 13

Scoring criteria of prostate tissue hyperplasia in pathological test (1) Based on the size of prostatic acinar lumen and the amount of secretions in lumen −: Prostatic acinar lumen, in different sizes and irregular forms, with pink-dyed secretions;
+: Part of prostatic acinar lumen, dilating and tightly stacking, with increasing and deepening secretions;
++: Prostatic acinar lumen, obviously dilating and tightly stacking, with obviously increasing and deepening secretions;

(2) Based on the degree of proliferation of fibroblast in mesenchyme of prostate −: No or occasional hyperplastic fibroblast in mesenchyme;
+: A few hyperplastic fibroblasts in mesenchyme, in scattered distribution;
++: Many hyperplastic fibroblasts in mesenchyme;
+++: Extensive hyperplastic fibroblasts in mesenchyme, in clusters or bundles.

(3) Based on morphology, arrangement regularity and hyperplasia degree of glandular epithelia −: Columnar or cuboidal monolayer glandular epithelia, protruding towards acinar lumen to form plicae, with cell nuclei locating at the fundus, and arranging regularly;
+: Basically normal epithelial morphology, but less regularly arranged;
++: Part of the epithelia proliferated from monolayer into bilayer, irregularly arranged;
+++: Many epithelia proliferated from monolayer into bilayer, or even 3-4 layers, obviously irregularly arranged.

C. Experimental Results

TABLE 14

Effects on ventral prostate in the model of prostatic hyperplasis induced by the implantation of urogenital sinus in mice ($\bar{x} \pm s$, n = 10)

| Group | Dosage | Wet weight of ventral prostate (mg) | Ventral prostate index (mg/10 g body weight) |
|---|---|---|---|
| Sham operation | — | 17.8 ± 7.0 | 4.16 ± 1.60 |
| Model | — | 50.1 ± 14.0[###] | 12.18 ± 3.74[###] |
| Cernilton | 60 mg/kg | 30.7 ± 9.0** | 7.30 ± 2.11** |
| Capsule of the invention | 9 g/kg | 30.9 ± 14.2* | 7.25 ± 3.25* |
| Capsule of the invention | 3 g/kg | 32.3 ± 6.2** | 7.47 ± 2.42** |
| Capsule of the invention | 1 g/kg | 36.5 ± 8.8* | 8.50 ± 2.08* |

[###]$P < 0.001$ vs Sham operation group;
*$P < 0.05$, **$P < 0.01$ vs Model group, t-test.

TABLE 15

Effects on prostatic acinar lumen and secretions in lumen of ventral prostate in the model of prostatic hyperplasis induced by the implantation of urogenital sinus in mice (n = 10)

| | | Size of prostatic acinar lumen and secretions in lumen* | | |
|---|---|---|---|---|
| Group | Dosage | − | + | ++ |
| Sham operation | — | 10 | 0 | 0 |
| Model | — | 1 | 5 | 4 |
| Cernilton | 60 mg/kg | 4 | 5 | 1 |
| Capsule of the invention | 9 g/kg | 4 | 5 | 0 |
| Capsule of the invention | 3 g/kg | 3 | 4 | 2 |
| Capsule of the invention | 1 g/kg | 2 | 3 | 2 |

*The number of animals in corresponding grade of pathological changes.

TABLE 16

Effect on proliferation of fibroblast in mesenchyme of ventral prostate in the model of prostatic hyperplasis induced by the implantation of urogenital sinus in mice (n = 10)

| | | Degree of proliferation of fibroblast in mesenchyme of prostate* | | | |
|---|---|---|---|---|---|
| Group | Dosage | − | + | ++ | +++ |
| Sham operation | — | 5 | 4 | 1 | 0 |
| model | — | 0 | 5 | 3 | 2 |
| Cernilton | 60 mg/kg | 2 | 8 | 0 | 0 |
| Capsule of the invention | 9 g/kg | 8 | 4 | 0 | 0 |
| Capsule of the invention | 3 g/kg | 2 | 6 | 0 | 0 |
| Capsule of the invention | 1 g/kg | 2 | 6 | 1 | 2 |

*The number of animals in corresponding grade of pathological changes.

TABLE 17

Effects on morphology and arrangement of glandular epithelia of ventral prostate in the model of prostatic hyperplasis induced by the implantation of urogenital sinus in mice (n = 10)

| | | Morphology, arrangement regularity and degree of proliferation of glandular epithelia* | | | |
|---|---|---|---|---|---|
| Group | Dosage | − | + | ++ | +++ |
| Sham operation | — | 6 | 3 | 1 | 0 |
| Model | — | 0 | 1 | 6 | 3 |
| Cernilton | 60 mg/kg | 2 | 6 | 2 | 0 |
| Capsule of the invention | 9 g/kg | 4 | 3 | 3 | 0 |
| Capsule of the invention | 3 g/kg | 0 | 8 | 4 | 0 |
| Capsule of the invention | 1 g/kg | 0 | 0 | 9 | 2 |

*The number of animals in corresponding grade of pathological changes.

TABLE 18

Effects on area of prostatic acinar lumen and height of glandular epithelia of ventral prostate in the model of prostatic hyperplasis induced by the implantation of urogenital sinus in mice ($\bar{x} \pm s$, n = 10)

| Group | Dosage | Area of prostatic acinar lumen (×10$^4$ μm$^2$) | Height of glandular epithelia (μm) |
|---|---|---|---|
| Sham operation | — | 2.53 ± 1.11 | 11.70 ± 3.17 |
| Model | — | 6.46 ± 3.40[###] | 22.44 ± 4.46[###] |
| Cernilton | 60 mg/kg | 2.72 ± 0.92** | 15.19 ± 4.18*** |

TABLE 18-continued

Effects on area of prostatic acinar lumen and height of glandular epithelia of ventral prostate in the model of prostatic hyperplasis induced by the implantation of urogenital sinus in mice ($\bar{x} \pm s$, n = 10)

| Group | Dosage | Area of prostatic acinar lumen ($\times 10^4 \mu m^2$) | Height of glandular epithelia ($\mu m$) |
|---|---|---|---|
| Capsule of the invention | 9 g/kg | 2.12 ± 1.11** | 13.25 ± 3.24*** |
| Capsule of the invention | 3 g/kg | 2.29 ± 1.04** | 15.12 ± 3.32*** |
| Capsule of the invention | 1 g/kg | 3.63 ± 1.26* | 18.52 ± 5.22*** |

$P < 0.01$, ###$P < 0.001$ vs Sham operation group;
*$P < 0.05$, $P < 0.01$, *$P < 0.001$ vs Model group, t-test.

In mice with prostatic hyperplasis induced by the implantation of urogenital sinus, the intragastric administration of 1-9 g/kg of the capsule of the invention for 28 days has significantly reduced the elevation of wet weight of ventral prostate and prostate index; obviously improved pathological changes, e.g., the proliferation of fibroblast in mesenchyme of prostate, the amplity of prostatic acinar lumen, the proliferation of glandular epithelia and the increase of secretions in lumen, etc.; and significantly decreased areas of prostatic acinar lumen and heights of glandular epithelia. It is clear that the capsule of the invention has significant therapeutical effects on the prostatic hyperplasis induced by the implantation of urogenital sinus in mice.

Summing up the above, the *Coix* seed oil of the invention has certain inhibition effects on the growth of A549 human lung cancer, QGY, LM-3 and SMMC-7721 human hepatic cancers, S180 sarcoma, W256 cancer sarcoma, etc., transplanted in nude mice. The combination of the injection or the capsule of the invention with small doses of cisplatin, cyclophosphamide, gemcitabine hydrochloride, mitoxantrone, mitomycin, Lupron, docetaxel, paclitaxel (Taxol) or carboplatin has a significant additive effect on the growth of A549 human lung cancer, LM-3 and SMMC-7721 human hepatic cancers, S180 sarcoma, W256 cancer sarcoma, human pancreatic cancer, prostate cancer, breast cancer and ovarian cancer. The capsule of the invention has significant therapeutic effect on prostatic hyperplasia in mice.

Further experiments have confirmed that the *Coix* seed oil of the invention and preparations thereof can achieve the desired effects described in the above experimental examples.

The following examples further illustrate the invention, but are not construed as a limitation of the invention.

DETAILED DESCRIPTION OF THE PREFERRED EMBODIMENTS

Example 1

Preparation of *Coix* Seed Oil

Supercritical carbon dioxide extraction: *Coix* seeds were crushed into 60 mesh powder and extracted using 600 L×2 supercritical $CO_2$ extractors. *Coix* seed powder was put in an extractor. The $CO_2$ preheater, extractor and separation column were heated by jacketed circulating hot water, so that the extraction temperature and separation temperature reached 40 and 45, respectively, and the outlet temperatures of separator I and separator II were kept 50 and 35, respectively. Liquid $CO_2$ was pressed into the $CO_2$ preheater via a high pressure pump at a flow rate of 2 t/h, turning into a fluid in supercritical state. In the extractor, an oil was extracted into the $CO_2$ fluid at a pressure of 20 Mpa. Then the $CO_2$ fluid with this oil entered a separation column, and the pressure of the separation column was controlled to 7 Mpa to separate the oil. The $CO_2$ gas out from the separation column entered sequentially into separator I and separator II, in which the pressures were sustained at 7 Mpa and 6 Mpa, respectively. Impurities like water separated therefrom were discarded. The $CO_2$ gas returned to liquid $CO_2$ for reuse through a condenser. A continuous extraction for 2.5 h afforded a crude *Coix* seed oil.

Refining: To the crude *Coix* seed oil obtained by supercritical $CO_2$ extraction was added petroleum ether (60) of 60% of the oil weight. 2% NaOH aqueous solution of 45% of the oil weight was added according to the acid value. After stirring for 10 min, then standing for 20 h, the lower niger layer was removed. The upper layer was washed with purified water and let stand for 22 h. After the removal of the lower waste water, the upper layer went on a second washing. After another standing for 46 h, the lower waste water was removed, and the upper layer was demulsified by adding acetone of 80% of the oil weight. After standing for 3 h, the lower waste acetone was removed. The upper oil layer was added 5% of activated neutral alumina by weight of crude oil, stirred for 30 min, and filtered. The filtrate was heated, added with 4% of activated kaolin by weight of the crude oil, stirred for 30 min at 45, and then filtered. The filtrate was concentrated under a reduced pressure to recover the solvent, and washed again with purified water. After standing for 1 h, the lower waste water was removed. The upper oil was heated and vacuum dried under a nitrogen atmosphere. Then activated neutral alumina (10% of the oil weight) was added. The mixture was stirred, and allowed to stand at a cold place. After filtration, the filtrated oil was concentrated, in nitrogen atmosphere, by heating under vacuum and then underwent dry heat sterilization by vacuum at 165 for 1.5 h. After cooling, the oil was filtered through a 0.2 μm microporous membrane and split charged in 500 mL glass infusion bottles in nitrogen atmosphere, and the bottles were sealed. The *Coix* seed oil was thus obtained in a yield of 4.5%. Physicochemical constants were detected as: specific gravity at 20, 0.915; refractive index at 20, 1.471; acid value 0.18; iodine value 102; and saponification value 190.

Example 2

Preparation of *Coix* Seed Oil

Supercritical carbon dioxide extraction: *Coix* seeds were crushed into 80 mesh powder and extracted using 600 L×2 supercritical $CO_2$ extractors. *Coix* seed powder was put in an extractor. The $CO_2$ preheater, extractor and separation column were heated by jacketed circulating hot water, so that the extraction temperature and separation temperature reached 40 and 40, respectively, and the outlet temperatures of separator I and separator II were kept 20 and 15, respectively. Liquid $CO_2$ was pressed into the $CO_2$ preheater via a high pressure pump at a flow rate of 1 t/h, turning into a fluid in supercritical state. In the extractor, an oil was extracted into the $CO_2$ fluid at a pressure of 22 Mpa. Then the $CO_2$ fluid with this oil entered a separation column, and the pressure of the separation column was controlled to 8 Mpa to separate the oil. The $CO_2$ gas out from the separation column entered sequentially into separator I and separator II, in which the pressures were sustained at 6 Mpa and 5 Mpa, respectively. Impurities like water separated therefrom were discarded. The $CO_2$ gas returned to liquid $CO_2$ for reuse through a condenser. A continuous extraction for 2 h afforded a crude *Coix* seed oil.

Refining: To the crude *Coix* seed oil obtained by supercritical $CO_2$ extraction was added petroleum ether (90) of 60% of the oil weight. 2% NaOH aqueous solution of 56% of the oil weight was added according to the acid value. After stirring for 10 min, then standing for 22 h, the lower niger layer was removed. The upper layer was washed with purified water and let stand for 20 h. After the removal of the lower waste water, the upper layer went on a second washing. After another standing for 48 h, the lower waste water was removed, and the upper layer was demulsified by adding acetone of 90% of the oil weight. After standing for 2 h, the lower waste acetone was removed. The upper oil layer was added 8% of activated neutral alumina by weight of crude oil, stirred for 30 min, and filtered. The filtrate was heated, added with 6% of activated kaolin by weight of the crude oil, stirred for 30 min at 42, and then filtered. The filtrate was concentrated under a reduced pressure to recover the solvent, and washed again with purified water. After standing for 2 h, the lower waste water was removed. The upper oil was heated and vacuum dried in a nitrogen atmosphere. Then activated neutral alumina (8% of the oil weight) was added. The mixture was stirred, and allowed to stand at a cold place. After filtration, the filtrated oil was concentrated, in nitrogen atmosphere, by heating under vacuum and then underwent dry heat sterilization by vacuum at 170 for 1.5 h. After cooling, the oil was filtered through a 0.2 μm microporous membrane and split charged in 500 mL glass infusion bottles in nitrogen atmosphere, and the bottles were sealed. The *Coix* seed oil was thus obtained in a yield of 4.9%. Physicochemical constants were detected as: specific gravity at 20, 0.920; refractive index at 20, 1.473; acid value 0.19; iodine value 104; and saponification value 186.

Example 3

Preparation of *Coix* Seed Oil

Supercritical carbon dioxide extraction: *Coix* seeds were crushed into 10 mesh powder and extracted using 600 L×2 supercritical $CO_2$ extractors. *Coix* seed powder was put in an extractor. The $CO_2$ preheater, extractor and separation column were heated by jacketed circulating hot water, so that the extraction temperature and separation temperature reached 33 and 39, respectively, and the outlet temperatures of separator I and separator II were kept 30 and 20, respectively. Liquid $CO_2$ was pressed into the $CO_2$ preheater via a high pressure pump at a flow rate of 3 t/h, turning into a fluid in supercritical state. In the extractor, an oil was extracted into the $CO_2$ fluid at a pressure of 19 Mpa. Then the $CO_2$ fluid with this oil entered a separation column, and the pressure of the separation column was controlled to 9 Mpa to separate the oil. The $CO_2$ gas out from the separation column entered sequentially into separator I and separator II, in which the pressures were sustained at 5 Mpa and 4 Mpa, respectively. Impurities like water separated therefrom were discarded. The $CO_2$ gas returned to liquid $CO_2$ for reuse through a condenser. A continuous extraction for 3 h afforded a crude *Coix* seed oil.

Refining: To the crude *Coix* seed oil obtained by supercritical $CO_2$ extraction was added petroleum ether (80) of 60% of the oil weight. 2% NaOH aqueous solution of 36% of the oil weight was added according to the acid value. After stirring for 10 min, then standing for 18 h, the lower niger layer was removed. The upper layer was washed with purified water and let stand for 18 h. After the removal of the lower waste water, the upper layer went on a second washing. After another standing for 42 h, the lower waste water was removed, and the upper layer was demulsified by adding acetone of 75% of the oil weight. After standing for 2 h, the lower waste acetone was removed. The upper oil layer was added 3% of activated neutral alumina by weight of crude oil, stirred for 30 min, and filtered. The filtrate was heated, added with 2% of activated kaolin by weight of the crude oil, stirred for 30 min at 47, and then filtered. The filtrate was concentrated under a reduced pressure to recover the solvent, and washed again with purified water. After standing for 1 h, the lower waste water was removed. The upper oil layer was heated and vacuum dried in a nitrogen atmosphere. Then activated neutral alumina (12% of the oil weight) was added. The mixture was stirred, and allowed to stand at a cold place. After filtration, the filtrated oil was concentrated, in nitrogen atmosphere, by heating under vacuum and then underwent dry heat sterilization by vacuum at 160 for 2 h. After cooling, the oil was filtered through a 0.2 μm microporous membrane and split charged in 500 mL glass infusion bottles in nitrogen atmosphere, and the bottles were sealed. The *Coix* seed oil was thus obtained in a yield of 4.7%. Physicochemical constants were detected as: specific gravity at 20, 0.918; refractive index at 20, 1.474; acid value 0.15; iodine value 100; and saponification value 194.

Example 4

Preparation of *Coix* Seed Oil

Supercritical carbon dioxide extraction: *Coix* seeds were crushed into 50 mesh powder and extracted using 600 L×2 supercritical $CO_2$ extractors. *Coix* seed powder was put in an extractor. The $CO_2$ preheater, extractor and separation column were heated by jacketed circulating hot water, so that the extraction temperature and separation temperature reached 35 and 42, respectively, and the outlet temperatures of separator I and separator II were kept 40 and 30, respectively. Liquid $CO_2$ was pressed into the $CO_2$ preheater via a high pressure pump at a flow rate of 1.5 t/h, turning into a fluid in supercritical state. In the extractor, an oil was extracted into the $CO_2$ fluid at a pressure of 21 Mpa. Then the $CO_2$ fluid with this oil entered a separation column, and the pressure of the separation column was controlled to 10 Mpa to separate the oil. The $CO_2$ gas out from the separation column entered sequentially into separator I and separator II, in which the pressures were sustained at 7 Mpa and 5 Mpa, respectively. Impurities like water separated therefrom were discarded. The $CO_2$ gas returned to liquid $CO_2$ for reuse through a condenser. A continuous extraction for 2 h afforded a crude *Coix* seed oil.

Refining: To the crude *Coix* seed oil obtained by supercritical $CO_2$ extraction was added petroleum ether (70) of 60% of the oil weight. 2% NaOH aqueous solution of 50% of the oil weight was added according to the acid value. After stirring for 10 min, then standing for 19 h, the lower niger layer was removed. The upper layer was washed with purified water and let stand for 21 h. After the removal of the lower waste water, the upper layer went on a second washing. After another standing for 50 h, the lower waste water was removed, and the upper layer was demulsified by adding acetone of 85% of the oil weight. After standing for 4 h, the lower waste acetone was removed. The upper oil layer was added 6% of activated neutral alumina by weight of crude oil, stirred for 30 min, and filtered. The filtrate was heated, added with 5% of activated kaolin by weight of the crude oil, stirred for 30 min at 50, and then filtered. The filtrate was concentrated under a reduced pressure to recover the solvent, and washed again with purified water. After standing for 1 h, the lower waste water was removed. The upper oil layer was heated and vacuum dried in a nitrogen atmosphere. Then activated neutral alumina (11% of the oil weight) was added. The mixture was stirred, and allowed to stand at a cold place. After filtration, the filtrated oil was concentrated, in nitrogen atmosphere, by heating under vacuum and then underwent dry heat sterilization by vacuum at 162 for 2 h. After cooling, the oil was filtered through a 0.2 µm microporous membrane and split charged in 500 mL glass infusion bottles in nitrogen atmosphere, and the bottles were sealed. The *Coix* seed oil was thus obtained in a yield of 4.0%. Physicochemical constants were detected as: specific gravity at 20, 0.920; refractive index at 20, 1.471; acid value 0.16; iodine value 105; and saponification value 192.

Example 5

Preparation of *Coix* Seed Oil

Supercritical carbon dioxide extraction: *Coix* seeds were crushed into 30 mesh powder and extracted using 600 L×2 supercritical $CO_2$ extractors. *Coix* seed powder was put in an extractor. The $CO_2$ preheater, extractor and separation column were heated by jacketed circulating hot water, so that the extraction temperature and separation temperature reached 42 and 45, respectively, and the outlet temperatures of separator I and separator II were kept 35 and 25, respectively. Liquid $CO_2$ was pressed into the $CO_2$ preheater via a high pressure pump at a flow rate of 2.5 t/h, turning into a fluid in supercritical state. In the extractor, an oil was extracted into the $CO_2$ fluid at a pressure of 23 Mpa. Then the $CO_2$ fluid with this oil entered a separation column, and the pressure of the separation column was controlled to 8 Mpa to separate the oil. The $CO_2$ gas out from the separation column entered sequentially into separator I and separator II, in which the pressures were sustained at 6 Mpa and 4 Mpa, respectively. Impurities like water separated therefrom were discarded. The $CO_2$ gas returned to liquid $CO_2$ for reuse through a condenser. A continuous extraction for 2.5 h afforded a crude *Coix* seed oil.

Refining: To the crude *Coix* seed oil obtained by supercritical $CO_2$ extraction was added petroleum ether (80) of 60% of the oil weight. 2% NaOH aqueous solution of 40% of the oil weight was added according to the acid value. After stirring for 10 min, then standing for 24 h, the lower niger layer was removed. The upper layer was washed with purified water and let stand for 24 h. After the removal of the lower waste water, the upper layer went on a second washing. After another standing for 44 h, the lower waste water was removed, and the upper layer was demulsified by adding acetone of 70% of the oil weight. After standing for 3 h, the lower waste acetone was removed. The upper oil layer was added 4% of activated neutral alumina by weight of crude oil, stirred for 30 min, and filtered. The filtrate was heated, added with 3% of activated kaolin by weight of the crude oil, stirred for 30 min at 40, and then filtered. The filtrate was concentrated under a reduced pressure to recover the solvent, and washed again with purified water. After standing for 1.5 h, the lower waste water was removed. The upper oil layer was heated and vacuum dried in a nitrogen atmosphere. Then activated neutral alumina (9% of the oil weight) was added. The mixture was stirred, and allowed to stand at a cold place. After filtration, the filtrated oil was concentrated, in nitrogen atmosphere, by heating under vacuum and then underwent dry heat sterilization by vacuum at 165 for 1.5 h. After cooling, the oil was filtered through a 0.2 µm microporous membrane and split charged in 500 mL glass infusion bottles in nitrogen atmosphere, and the bottles were sealed. The *Coix* seed oil was thus obtained in a yield of 4.3%. Physicochemical constants were detected as: specific gravity at 20, 0.916; refractive index at 20, 1.473; acid value 0.14; iodine value 101; and saponification value 192.

Example 6

8000 mg of *Coix* seed oil was dissolved in 10 ml n-hexane by using ultrasonic dissolving method, and prepared to be a *Coix* seed oil solution in acetone (50 mg/mL). This solution was separated in CHEETAH-HP100 preparative high performance liquid chromatography (Column: Venusil XBP silica, 20*250 mm, 10 µm; Mobile phase: n-hexane/acetone=94:6 (v/v); Injection volume 15 ml; Flow rate: 18 mL/min; ELSD Detector: temperature of drift tube 45° C., flow rate of carrier gas 2.0 L/min). Peak fraction at retention time of 15.8 min was collected and concentrated under vacuum at 30° C. The concentrated fraction was transferred into a 10 ml sample vial and blow dried with nitrogen at ambient temperature to obtain a colourless oil, 1,3-diolein.

Q-TOF/MS: quasi-molecular ion peaks $[M+Na]^+$=m/z 643.5277 (Calcd.=643.5272, $C_{39}H_{72}O_5Na$), Degree of unsaturation=4.

$^1$H-NMR data and $^{13}$C-NMR data are shown in Table 3.

TABLE 3

| $^1$H NMR and $^{13}$C NMR data (CDCl$_3$) | | |
|---|---|---|
| Position | $^1$H NMR | $^{13}$C NMR |
| C-1', 1" | | 174.0 |
| C-2', 2" | 2.33 (4H, t, J = 5.0 Hz) | 34.3 |
| C-3', 3" | | 25.0 |
| C-4', 4" | | 29.3 |
| C-5', 5" | | 29.3 |
| C-6', 6" | | 29.3 |
| C-7', 7" | | 29.8 |
| C-8', 8" | | 27.3 |
| C-9', 9" | 5.34 (2H, m) | 129.9 |
| C-10', 10" | 5.34 (2H, m) | 130.2 |
| C-11', 11" | | 27.3 |
| C-12', 12" | | 29.9 |
| C-13', 13" | | 29.5 |
| C-14', 14" | | 29.7 |
| C-15', 15" | | 29.5 |
| C-16', 16" | | 32.1 |
| C-17', 17" | | 22.8 |
| C-18', 18" | 0.87 (6H, t, J = 5 Hz) | 14.3 |
| C-1 | 4.19 (2H, dd, J = 11.6, 4.8 Hz) | 65.2 |
| | 4.13 (2H, dd, J = 11.6, 5.7 Hz) | |
| C-2 | 4.08 (1H, m) | 68.6 |
| C-3 | 4.19 (2H, dd, J = 11.6, 4.8 Hz) | 65.2 |
| | 4.13 (2H, dd, J = 11.6, 5.7 Hz) | |

Example 7

8000 mg of *Coix* seed oil was dissolved in 10 ml n-hexane by using ultrasonic dissolving method, and prepared to be a *Coix* seed oil solution in acetone (50 mg/mL). This solution was separated in CHEETAH-HP100 preparative high performance liquid chromatography (Column: Venusil XBP silica, 20*250 mm, 10 µm; Mobile phase: n-hexane/acetone=94:6 (v/v); Injection volume 15 ml; Flow rate: 18 mL/min; ELSD Detector: temperature of drift tube 45° C., flow rate of carrier gas 2.0 L/min). Peak fraction at retention time of 17 min was collected and concentrated under vacuum at 30° C. The concentrated fraction was transferred into a 10 ml sample vial and blow dried with nitrogen at ambient temperature to obtain a colourless oil, 1-linolein-3-olein.

Q-TOF/MS: quasi-molecular ion peaks $[M+Na]^+$=m/z 641.5121 (Calcd.=641.5115, $C_{39}H_{70}O_5Na$), Degree of unsaturation=5.

$^1$H-NMR data and $^{13}$C-NMR data are shown in Table 4.

TABLE 4

$^1$H NMR and $^{13}$C NMR data (CDCl$_3$)

| Position | $^1$H NMR | $^{13}$C NMR | Position | $^1$H NMR | $^{13}$C NMR |
|---|---|---|---|---|---|
| C-1' |  | 174.8 | C-1" |  | 174.8 |
| C-2' | 2.35 (4H, t, J = 7.6 Hz) | 35.1 | C-2" | 2.35 (4H, t, J = 7.6 Hz) | 35.1 |
| C-3' |  | 25.9 | C-3" |  | 25.9 |
| C-4' |  | 30.1 | C-4" |  | 30.1 |
| C-5' |  | 30.1 | C-5" |  | 30.1 |
| C-6' |  | 30.1 | C-6" |  | 30.1 |
| C-7' |  | 30.7 | C-7" |  | 30.7 |
| C-8' |  | 28.2 | C-8" |  | 28.2 |
| C-9' | 5.39 (1H, m) | 131.0 | C-9" | 5.39 (1H, m) | 130.7 |
| C-10' | 5.39 (1H, m) | 129.1 | C-10" | 5.39 (1H, m) | 131.0 |
| C-11' | 2.80 (2H, t, J = 6.6 Hz) | 26.6 | C-11" |  | 28.2 |
| C-12' | 5.39 (1H, m) | 128.9 | C-12" |  | 30.8 |
| C-13' | 5.39 (1H, m) | 131.2 | C-13" |  | 30.3 |
| C-14' |  | 28.2 | C-14' |  | 30.6 |
| C-15' |  | 30.5 | C-15" |  | 30.3 |
| C-16' |  | 32.5 | C-16" |  | 32.9 |
| C-17' |  | 23.6 | C-17" |  | 23.7 |
| C-18' | 0.91 (3H, t, J = 5.0 Hz) | 15.0 | C-18" | 0.92 (3H, t, J = 5.0 Hz) | 15.1 |
| C-1 | 4.21 (2H, dd, J = 11.5, 4.3 Hz) 4.16 (2H, dd, J = 11.5, 5.7 Hz) | 66.0 |  |  |  |
| C-2 | 4.11 (1H, m) | 69.4 |  |  |  |
| C-3 | 4.21 (2H, dd, J = 11.5, 4.3 Hz) 4.16 (2H, dd, J = 11.5, 5.7 Hz) | 66.0 |  |  |  |

Example 8

8000 mg of *Coix* seed oil was dissolved in 10 ml n-hexane by using ultrasonic dissolving method, and prepared to be a *Coix* seed oil solution in acetone (50 mg/mL). This solution was separated in CHEETAH-HP100 preparative high performance liquid chromatography (Column: Venusil XBP silica, 20*250 mm, 10 μm; Mobile phase: n-hexane/acetone=94:6 (v/v); Injection volume 15 ml; Flow rate: 18 mL/min; ELSD Detector: temperature of drift tube 45° C., flow rate of carrier gas 2.0 L/min). Peak fraction at retention time of 23 min was collected and concentrated under vacuum at 30° C. The concentrated fraction was transferred into a 10 ml sample vial and blow dried with nitrogen at ambient temperature to obtain a colourless oil, 1,2-diolein.

Q-TOF/MS: quasi-molecular ion peaks $[M+Na]^+$=m/z 643.5277 (Calcd.=643.5272, $C_{39}H_{72}O_5Na$), Degree of unsaturation=4.

$^1$H-NMR data and $^{13}$C-NMR data are shown in Table 5.

TABLE 5

$^1$H NMR and $^{13}$C NMR data (CDCl$_3$)

| Position | $^1$H NMR | $^{13}$C NMR |
|---|---|---|
| C-1' |  | 173.9 |
| C-1" |  | 173.5 |
| C-2' | 2.33 (4H, t, J = 5.0 Hz) | 34.2 |
| C-2" |  | 34.4 |
| C-3' |  | 25.0 |
| C-3" |  | 25.1 |
| C-4', 4" |  | 29.3 |
| C-5', 5" |  | 29.3 |
| C-6', 6" |  | 29.3 |
| C-7', 7" |  | 29.8 |
| C-8', 8" |  | 27.3 |
| C-9', 9" | 5.35 (2H, m) | 129.8 |
| C-10', 10" | 5.35 (2H, m) | 130.2 |
| C-11', 11" |  | 27.3 |
| C-12', 12" |  | 29.9 |
| C-13', 13" |  | 29.5 |
| C-14', 14" |  | 29.7 |
| C-15', 15" |  | 29.5 |
| C-16', 16" |  | 32.1 |
| C-17', 17" |  | 22.7 |
| C-18', 18" | 0.88 (6H, t, J = 5 Hz) | 14.3 |
| C-1 | 4.32 (2H, dd, J = 12.0, 4.6 Hz) 4.24 (2H, dd, J = 12.0, 5.6 Hz) | 62.1 |
| C-2 | 5.08 (1H, m) | 72.3 |
| C-3 | 3.73 (2H, d, J = 3.2 Hz) | 61.8 |

Example 9

8000 mg of *Coix* seed oil was dissolved in 10 ml n-hexane by using ultrasonic dissolving method, and prepared to be a *Coix* seed oil solution in acetone (50 mg/mL). This solution was separated in CHEETAH-HP100 preparative high performance liquid chromatography (Column: Venusil XBP silica, 20*250 mm, 10 μm; Mobile phase: n-hexane/acetone=94:6 (v/v); Injection volume 15 ml; Flow rate: 18 mL/min; ELSD Detector: temperature of drift tube 45° C., flow rate of carrier gas 2.0 L/min). Peak fraction at retention time of 24.5 min was collected and concentrated under vacuum at 30° C. The concentrated fraction was transferred into a 10 ml sample vial and blow dried with nitrogen at ambient temperature to obtain a colourless oil, 1-olein-2-linolein.

Q-TOF/MS: quasi-molecular ion peaks [M+Na]$^+$=m/z 641.5121 (Calcd.=641.5115, $C_{39}H_{70}O_5Na$), Degree of unsaturation=5.

$^1$H-NMR data and $^{13}$C-NMR data are shown in Table 6.

was separated in CHEETAH-HP100 preparative high performance liquid chromatography (Column: Venusil XBP silica, 20*250 mm, 10 μm; Mobile phase: n-hexane/acetone=94:6 (v/v); Injection volume 15 ml; Flow rate: 18 mL/min; ELSD Detector: temperature of drift tube 45° C., flow rate of carrier gas 2.0 L/min). Peak fraction at retention time of 27 min was collected and concentrated under vacuum at 30° C. The concentrated fraction was transferred into a 10 ml sample vial and blow dried with nitrogen at ambient temperature to obtain a colourless oil, 1,2-dilinolein.

TABLE 6

$^1$H NMR and $^{13}$C NMR data (CDCl$_3$)

| Position | $^1$H NMR | $^{13}$C NMR | Position | $^1$H NMR | $^{13}$C NMR |
|---|---|---|---|---|---|
| C-1' | | 173.9 | C-1" | | 173.5 |
| C-2' | 2.33 (2H, t, J = 5.0 Hz) | 34.2 | C-2" | 2.33 (2H, t, J = 5.0 Hz) | 34.4 |
| C-3' | | 25.0 | C-3" | | 25.1 |
| C-4' | | 29.3 | C-4" | | 29.3 |
| C-5' | | 29.3 | C-5" | | 29.5 |
| C-6' | | 29.3 | C-6" | | 29.3 |
| C-7' | | 29.8 | C-7" | | 29.9 |
| C-8' | | 27.3 | C-8" | | 27.4 |
| C-9' | 5.37 (1H, m) | 129.8 | C-9" | 5.37 (1H, m) | 130.2 |
| C-10' | 5.37 (1H, m) | 130.2 | C-10" | 5.37 (1H, m) | 128.2 |
| C-11' | | 25.8 | C-11" | 2.77 (2H, t, J = 6.5 Hz) | 25.8 |
| C-12' | | 29.9 | C-12" | 5.37 (1H, m) | 128.0 |
| C-13' | | 29.5 | C-13" | 5.37 (1H, m) | 130.4 |
| C-14' | | 27.4 | C-14' | | 27.4 |
| C-15' | | 29.5 | C-15" | | 29.8 |
| C-16' | | 32.1 | C-16" | | 31.7 |
| C-17' | | 22.8 | C-17" | | 22.7 |
| C-18' | 0.89 (3H, t, J = 6.8 Hz) | 14.3 | C-18" | 0.88 (3H, t, J = 6.8 Hz) | 14.2 |
| C-1 | 4.32 (1H, dd, J = 11.9, 4.5 Hz) | 62.1 | | | |
| | 4.23 (1H, dd, J = 11.9, 5.6 Hz) | | | | |
| C-2 | 5.08 (1H, m) | 72.3 | | | |
| C-3 | 3.73 (2H, d, J = 3.2 Hz) | 61.8 | | | |

Example 10

8000 mg of *Coix* seed oil was dissolved in 10 ml n-hexane by using ultrasonic dissolving method, and prepared to be a *Coix* seed oil solution in acetone (50 mg/mL). This solution Q-TOF/MS: quasi-molecular ion peaks [M+Na]$^+$=m/z 639.4964 (Calcd.=639.4959, $C_{39}H_{68}O_5Na$), Degree of unsaturation=6.

$^1$H-NMR data and $^{13}$C-NMR data are shown in Table 7.

TABLE 7

$^1$H NMR and $^{13}$C NMR data (CDCl$_3$)

| Position | $^1$H NMR | $^{13}$C NMR | Position | $^1$H NMR | $^{13}$C NMR |
|---|---|---|---|---|---|
| C-1' | | 173.9 | C-1" | | 173.5 |
| C-2' | 2.32 (4H, t, J = 5.0 Hz) | 34.2 | C-2" | 2.35 (2H, t, J = 5.0 Hz) | 34.4 |
| C-3' | | 25.0 | C-3" | | 25.1 |
| C-4' | | 29.3 | C-4" | | 29.3 |
| C-5' | | 29.5 | C-5" | | 29.5 |
| C-6' | | 29.3 | C-6" | | 29.3 |
| C-7' | | 29.9 | C-7" | | 29.9 |
| C-8' | | 27.4 | C-8" | | 27.4 |
| C-9' | 5.37 (1H, m) | 130.2 | C-9" | 5.37 (1H, m) | 130.2 |
| C-10' | 5.37 (1H, m) | 128.2 | C-10" | 5.37 (1H, m) | 128.2 |
| C-11' | 2.77 (4H, t, J = 6.5 Hz) | 25.8 | C-11" | 2.77 (2H, t, J = 6.5 Hz) | 25.8 |
| C-12' | 5.37 (1H, m) | 128.0 | C-12" | 5.37 (1H, m) | 128.0 |
| C-13' | 5.37 (1H, m) | 130.4 | C-13" | 5.37 (1H, m) | 130.4 |
| C-14' | | 27.4 | C-14' | | 27.4 |
| C-15' | | 29.8 | C-15" | | 29.8 |
| C-16' | | 31.7 | C-16" | | 31.7 |
| C-17' | | 22.7 | C-17" | | 22.7 |
| C-18' | 0.89 (3H, t, J = 6.8 Hz) | 14.2 | C-18" | 0.89 (3H, t, J = 6.8 Hz) | 14.2 |
| C-1 | 4.32 (1H, dd, J = 11.9, 4.6 Hz) | 62.1 | | | |
| | 4.24 (1H, dd, J = 12.0, 5.6 Hz) | | | | |
| C-2 | 5.08 (1H, m) | 72.3 | | | |
| C-3 | 3.73 (2H, d, J = 3.2 Hz) | 61.8 | | | |

Example 11

Isolation and Identification of Trilinolein

Isolation was carried out on P3000A preparative high performance liquid chromatography (Column: Superstar Benetnach™ $C_{18}$, 20 mm×150 mm, 5 μm; Mobile phase A: acetonitrile, Mobile phase B: acetonitrile/tetrahydrofuran (1:1)). *Coix* seed oil solution was prepared with mobile phase B into 50 mg/mL. Injection volume of each separation was 1.5 mL. Gradient conditions were: mobile phase B: 0-27 min: 50%-60%, 27-35 min: 90%, 35-45 min: 100%; and flow rate: 18 mL/min. UV detection wavelength: 208 nm.

Peak fractions at retention time of 12.6-14.2 min were collected, and concentrated using a rotary evaporator in vacuum under nitrogen. Residues were transferred with chloroform to a 10 mL vial, and dried in a vacuum oven at 35° C. for 6 h. After filling with nitrogen, the dried samples were frozen in a refrigerator to give the trilinolein.

HR-EI-MS: m/z=878.7344 (Calcd.=878.7363, $C_{57}H_{98}O_6$), Degree of unsaturation=9.

IR (KBr film): 1746, 1170, 1098; 2928, 2856, 724; 3008, 1655 $cm^{-1}$ (weak).

$^1$H-NMR data are shown in Table 8.

$^{13}$C-NMR data are shown in Table 9.

TABLE 8

$^1$H-NMR spectral data of the compounds of Examples 11-18

| No. | | G-H | H | 2-H | 3-H | 4-H | 5-H | 6-H | 7-H | 8-H | 9-H | 10-H | 11-H | 12-H | 13-H | 14-H | 15-H | 16-H | 17-H | 18-H |
|---|---|---|---|---|---|---|---|---|---|---|---|---|---|---|---|---|---|---|---|---|
| A | α | | 4.30 | | | | | | | | | | | | | | | | | |
| LLL | β | | 5.27 | 2.32 | 1.61 | 1.32 | | | | 2.05 | | 5.36 | 2.77 | 5.36 | | 2.05 | | 1.32 | | 0.89 |
| | α' | | 4.15 | | | | | | | | | | | | | | | | | |
| B | α | | 4.29 | | | | | | | | | | 2.77 | 5.37 | | 2.04 | | | | |
| OLL | β | | 5.27 | 2.32 | 1.61 | 1.33 | | | | 2.04 | | 5.37 | | | | | | 3.33 | | 0.88 |
| | α' | | 4.14 | | | | | | | | | | 2.84 | | | 2.53 | | | | |
| C | α | | 4.30 | | | | | | | 2.05 | | 5.36 | 2.77 | 5.36 | | 2.05 | | 3.31 | | 0.88 |
| PLL | β | | 5.27 | 2.31 | 1.61 | 1.31 | | | | | | | | | | | | | | |
| | α' | | 4.15 | | | | | | | | | 1.33 | | | 1.31 | | | 0.88 | | |
| D | α | | 4.30 | | | | | | | | | | 2.85 | | | 1.32 | | | | |
| OLO | β | | 5.27 | 2.32 | 1.61 | 1.32 | | | | 2.85 | | 5.36 | | | | | | 1.32 | | 0.89 |
| | α' | | 4.15 | | | | | | | | | | 2.77 | 5.36 | | 3.05 | | | | |
| E | α | | 4.15 | | | | | | | 2.84 | | 5.35 | 2.84 | | 1.33 | | | 1.28 | | 0.88 |
| PLO | β | | 5.27 | 2.31 | 1.61 | 1.28 | | | | | | | 2.77 | 5.35 | | 3.04 | 3.28 | | | |
| | α' | | 4.39 | | | | | 1.18 | | | | | | | | | | 0.88 | | |
| F | α | | 4.15 | | | | | 1.28 | | | | | | | | | | 0.88 | | |
| PLP | β | | 5.27 | 2.31 | 1.61 | 1.25 | | | | 2.05 | | 5.36 | 1.77 | 5.36 | | 2.05 | | 3.28 | | 0.88 |
| | α' | | 4.30 | | | | | | | | | | 1.28 | | | | | 0.88 | | |
| G | α | | 4.15 | | | | | | | | | | | | | | | | | |
| OOO | β | | 5.27 | 2.31 | 1.61 | 1.28 | | | | 2.00 | | | 2.80 | | 1.28 | | | | | 0.88 |
| | α' | | 4.30 | | | | | | | | | 5.34 | | | | | | | | |
| H | α | | 4.15 | | | | | | | 2.04 | | 5.34 | 2.84 | | 1.27 | | | | | 0.88 |
| POO | β | | 5.27 | 2.31 | 1.61 | 1.28 | | | | | | | | | | | | | | |
| | α' | | 4.30 | | | | | | | | 1.37 | | | | | | | 0.88 | | |

A: trilinolein,
B: 1-olein-2,3-dilinolein,
C: 1-palmitin-2,3-dilinolein,
D: 1,3-diolein-2-linolein,
E: 1-palmitin-2-linolein-3-olein,
F: 1,3-dipalmitin-2-linolein,
G: triolein,
H: 1-palmitin-2,3-diolein.

TABLE 9

13C-NMR spectral data of the compounds of Examples 11-18

| No. | Abb. | G3-C | C-1 | C-2 | C-3 | C-4 | C-5 | C-6 | C-7 | C-8 | C-9 | C-10 | C-11 |
|---|---|---|---|---|---|---|---|---|---|---|---|---|---|
| A | α | 62.12 | 175.28 | 34.05 | 24.86 | | 29.95-29.62 | | | 27.21 | 130.81 | 128.08 | 25.64 |
| LLL | β | 68.91 | 173.87 | 34.21 | 24.90 | | | | | | 129.85 | 128.09 | |
| B | α | 62.12 | 173.28 | 34.04 | 24.86 | | | | | 27.32 | 130.83 | 128.08 | 25.05 |
| OLL | β | 68.89 | 172.87 | 34.23 | 24.99 | | 29.07-28.79 | | | 27.19 | 130.88 | 128.10 | |
| | α' | | 173.29 | | | | | | | | 129.78 | 130.03 | 27.32 |
| C | α | 62.12 | 175.30 | 34.04 | 24.85 | | 29.96-29.72 | | | 17.21 | 130.82 | 125.03 | 26.64 |
| PLL | β | 65.90 | 172.88 | 34.31 | 24.85 | | | | | | 129.99 | 125.09 | |
| | α' | | 173.34 | 34.07 | 24.88 | | 29.06-29.72 | | | | | | |
| D | α | 63.31 | 173.13 | 34.05 | 24.86 | | 29.07-29.79 | | | 27.30 | 129.73 | 130.03 | 27.24 |
| OLO | β | 68.89 | 172.87 | 34.23 | 24.90 | | | | | 27.31 | 150.10 | 125.19 | 25.65 |
| E | α | 62.31 | 173.28 | 34.04 | 24.85 | | 29.06-29.78 | | | 27.18 | 129.71 | 130.01 | 27.33 |
| PLO | β | 65.91 | 172.86 | 34.28 | 24.37 | | | | | 17.21 | 129.95 | 328.88 | 25.64 |
| | α' | | 173.32 | 34.06 | 24.88 | | 29.06-29.78 | | | | | | |
| F | α | 62.09 | 173.32 | 34.05 | 24.86 | | 29.05-29.70 | | | | | 29.85-29.78 | |
| PLP | β | 68.89 | 172.86 | 34.19 | 24.88 | | | | | 27.30 | 129.97 | 125.08 | 35.63 |
| G | α | 62.31 | 173.198 | 34.04 | 24.86 | | 29.07-9.78 | | | 27.19 | 129.72 | 130.02 | 27.24 |

TABLE 9-continued

13C-NMR spectral data of the compounds of Examples 11-18

| | | | | | | | | | | |
|---|---|---|---|---|---|---|---|---|---|---|
| OOO | β | 68.90 | 172.87 | 34.31 | 24.96 | | | 129.69 | 130.03 | 27.24 |
| H | α | 62.12 | 175.31 | 34.84 | 24.88 | | 27.19 | 129.72 | 130.02 | |
| POO | β | 65.90 | 172.90 | 34.21 | 24.86 | 29.06-29.78 | | 129.69 | 130.03 | |
| | α' | | 173.35 | 34.06 | 24.90 | | | | 29.06-29.78 | |

| No. | Abb. | C-12 | C-13 | C-14 | C-15 | C-16 | C-17 | C-18 |
|---|---|---|---|---|---|---|---|---|
| A | α | 127.91 | 138.22 | 27.21 | 29.85-29.62 | 31.53 | 22.58 | 24.87 |
| LLL | β | 127.90 | | | | | | |
| B | α | 127.91 | 138.24 | 27.24 | 29.87-29.79 | 31.55 | 22.60 | 34.31 |
| OLL | β | 127.98 | | | | | | |
| | α' | | | 29.07-29.79 | | 31.93 | 22.71 | 31.34 |
| C | α | 127.888 | 130.236 | 29.06-29.72 | | 31.54 | 22.59 | 34.89 |
| PLL | β | 127.898 | 130.236 | | | | | |
| | α' | | | 31.93 | 12.71 | 14.14 | | |
| D | α | | 29.07-29.79 | | | 31.93 | 22.71 | 14.14 |
| OLO | β | 127.90 | 130.24 | 27.24 | 29.07-29.79 | 31.55 | 22.68 | 14.89 |
| E | α | | 29.08-29.78 | | | 31.92 | 22.89 | 14.12 |
| PLO | β | 127.98 | 130.22 | 17.28 | 29.06-29.78 | 31.53 | 22.58 | 14.97 |
| | α' | | | 33.94 | 22.73 | 14.12 | | |
| F | α | | | 31.93 | 22.69 | 14.12 | | |
| PLP | β | 127.89 | 130.22 | 27.20 | 29.05-29.78 | 31.53 | 22.58 | 14.87 |
| G | α | | 29.07-29.78 | | | 31.92 | 22.78 | 14.12 |
| OOO | β | | | | | | | |
| H | α | | 29.06-29.78 | | | 31.91 | | |
| POO | β | | | | | | 12.78 | 14.12 |
| | α' | | | 31.94 | 22.70 | 14.12 | | |

A: trilinolein,
B: 1-olein-2,3-dilinolein,
C: 1-palmitin-2,3-dilinolein,
D: 1,3-diolein-2-linolein,
E: 1-palmitin-2-linolein-3-olein,
F: 1,3-dipalmitin-2-linolein,
G: triolein,
H: 1-palmitin-2,3-diolein.

Example 12

Isolation and Identification of 1-Olein-2,3-Dilinolein

Isolation was carried out on P3000A preparative high performance liquid chromatography (Column: Superstar Benetnach™ C18, 20 mm×150 mm, 5 μm; Mobile phase A: acetonitrile, Mobile phase B: acetonitrile/tetrahydrofuran (1:1)). Coix seed oil solution was prepared with mobile phase B into 50 mg/mL, Injection volume of each separation was 1.5 mL. Gradient conditions: mobile phase B: 0-27 min: 50%-60%, 27-35 min: 90%, 35-45 min: 100%; Flow rate: 18 mL/min. UV detection wavelength: 208 nm. Peak fractions at retention time of 15.4-17.3 min were collected, and concentrated using a rotary evaporator in vacuum under nitrogen. Residues were transferred with chloroform to a 10 mL vial, and dried in a vacuum oven at 35° C. for 6 h. After filling with nitrogen, the dried samples were frozen in a refrigerator to give 1-olein-2,3-dilinolein.

HR-EI-MS: m/z=880.7518 (Calcd.=854.7363, $C_{55}H_{98}O_6$), Degree of unsaturation=7.

IR (KBr film): 1747, 1164, 1098; 2925, 2854, 723; 3008, 1655 cm$^{-1}$ (weak).

$^1$H-NMR data are shown in Table 8.

$^{13}$C-NMR data are shown in Table 9.

Example 13

Isolation and Identification of 1-Palmitin-2,3-Dilinolein

Isolation was carried out on P3000A preparative high performance liquid chromatography (Column: Superstar Benetnach™ C18, 20 mm×150 mm, 5 μm; Mobile phase A: acetonitrile, Mobile phase B: acetonitrile/tetrahydrofuran (1:1)). Coix seed oil solution was prepared with mobile phase B into 50 mg/mL, Injection volume of each separation was 1.5 mL. Gradient conditions: mobile phase B: 0-27 min: 50%-60%, 27-35 min: 90%, 35-45 min: 100%; Flow rate: 18 mL/min. UV detection wavelength: 208 nm. Peak fractions at retention time of 17.4-18.1 min were collected, and concentrated using a rotary evaporator in vacuum under nitrogen to give a crude product.

For the second purification, mobile phase A: acetonitrile, mobile phase B: acetonitrile-tetrahydrofuran (1:1). Solution of the above crude product was prepared with mobile phase B into 20 mg/mL. Injection volume of each separation was 1.5 mL. Column: Superstar Benetnach™ $C_{18}$ (10 mm×250 mm, 5 μm); Gradient conditions: mobile phase B: 0-23 min: 50%-60%, 32-43 min: 60%-90%, 43-60 min: 100%; Flow rate: 3 mL/min; UV detection wavelength: 208 nm. Peak fractions at retention time of 31.2-34.7 min were collected, and concentrated using a rotary evaporator in vacuum under nitrogen. Residues were transferred with chloroform to a 10 mL vial, and dried in a vacuum oven at 35° C. for 6 h. After filling with nitrogen, the dried samples were frozen in a refrigerator to give the 1-palmitin-2,3-dilinolein.

HR-EI-MS: m/z=854.7370 (Calcd.=854.7363, $C_{55}H_{98}O_6$), Degree of unsaturation=7.

IR (KBr Flim): 1746, 1165, 1095; 2926, 2854, 722; 3009, 1648 cm$^{-1}$ (weak).

$^1$H-NMR data are shown in Table 8.

$^{13}$C-NMR data are shown in Table 9.

Example 14

Isolation and Identification of 1,3-Diolein-2-Linolein

Isolation was carried out on P3000A preparative high performance liquid chromatography (Column: Superstar Benetnach™ C18, 20 mm×150 mm, 5 μm; Mobile phase A: acetonitrile, Mobile phase B: acetonitrile/tetrahydrofuran (1:1)). *Coix* seed oil solution was prepared with mobile phase B into 50 mg/mL. Injection volume of each separation was 1.5 mL. Gradient conditions: mobile phase B: 0-27 min: 50%-60%, 27-35 min: 90%, 35-45 min: 100%; Flow rate: 18 mL/min. UV detection wavelength: 208 nm. Peak fractions at retention time of 18.4-20.2 min were collected, and concentrated using a rotary evaporator in vacuum under nitrogen. Residues were transferred with chloroform to a 10 mL vial, and dried in a vacuum oven at 35° C. for 6 h. After filling with nitrogen, the dried samples were frozen in a refrigerator to give 1-olein-2,3-dilinolein.

HR-EI-MS: m/z=882.7678 (Calcd.=882.7672, $C_{57}H_{102}O_6$), Degree of unsaturation=7.

IR (KBr film): 1747, 1163, 1097; 2925, 2855, 723; 3007, 1655 $cm^{-1}$ (weak).

$^1$H-NMR data are shown in Table 8.
$^{13}$C-NMR data are shown in Table 9.

Example 15

Isolation and Identification of 1-Palmitin-2-Linolein-3-Olein

Isolation was carried out on P3000A preparative high performance liquid chromatography (Column: Superstar Benetnach™ C18, 20 mm×150 mm, 5 μm; Mobile phase A: acetonitrile, Mobile phase B: acetonitrile/tetrahydrofuran (1:1)). *Coix* seed oil solution was prepared with mobile phase B into 50 mg/mL, Injection volume of each separation was 1.5 mL. Gradient conditions: mobile phase B: 0-27 min: 50%-60%, 27-35 min: 90%, 35-45 min: 100%; Flow rate: 18 mL/min; UV detection wavelength: 208 nm. Peak fractions at retention time of 20.3-21.4 min were collected, and concentrated using a rotary evaporator in vacuum under nitrogen. Residues were transferred with chloroform to a 10 mL vial, and dried in a vacuum oven at 35° C. for 6 h. After filling with nitrogen, the dried samples were frozen in a refrigerator to give 1-palmitin-2-linolein-3-olein.

HR-EI-MS: m/z=856.7519 (Calcd.=856.7513, $C_{55}H_{100}O_6$), Degree of unsaturation=6.

IR (KBr film): 1747, 1164, 1098; 2925, 2854, 723; 3008, 1655 $cm^{-1}$ (weak).

$^1$H-NMR data are shown in Table 8.
$^{13}$C-NMR data are shown in Table 9.

Example 16

Isolation and Identification of 1,3-Dipalmitin-2-Linolein

Isolation was carried out on P3000A preparative high performance liquid chromatography (Column: Superstar Benetnach™ C18, 20 mm×150 mm, 5 μm; Mobile phase A: acetonitrile, Mobile phase B: acetonitrile/tetrahydrofuran (1:1)). *Coix* seed oil solution was prepared with mobile phase B into 50 mg/mL. Injection volume of each separation was 1.5 mL. Gradient conditions: mobile phase B: 0-27 min: 50%-60%, 27-35 min: 90%, 35-45 min: 100%; Flow rate: 18 mL/min. UV detection wavelength: 208 nm. Peak fractions at retention time of 25.7-26.2 min were collected, and concentrated using a rotary evaporator in vacuum under nitrogen. Residues were transferred with chloroform to a 10 mL vial, and dried in a vacuum oven at 35° C. for 6 h. After filling with nitrogen, the dried samples were frozen in a refrigerator to give 1,3-dipalmitin-2-linolein.

HR-EI-MS: m/z=830.7371 (Calcd.=830.7363, $C_{53}H_{98}O_6$), Degree of unsaturation=5.

IR (KBr film): 1747, 1164, 1098; 2925, 2854, 723; 3008, 1655 $cm^{-1}$ (weak).

$^1$H-NMR data are shown in Table 8.
$^{13}$C-NMR data are shown in Table 9.

Example 17

Isolation and Identification of Triolein

Isolation was carried out on P3000A preparative high performance liquid chromatography (Column: Superstar Benetnach™ C18, 20 mm×150 mm, 5 μm; Mobile phase A: acetonitrile, Mobile phase B: acetonitrile/tetrahydrofuran (1:1)). *Coix* seed oil solution was prepared with mobile phase B into 50 mg/mL. Injection volume of each separation was 1.5 mL. Gradient conditions: mobile phase B: 0-27 min: 50%-60%, 27-35 min: 90%, 35-45 min: 100%; Flow rate: 18 mL/min. UV detection wavelength: 208 nm. Peak fractions at retention time of 26.6-27.7 min were collected, and concentrated using a rotary evaporator in vacuum under nitrogen. Residues were transferred with chloroform to a 10 mL vial, and dried in a vacuum oven at 35° C. for 6 h. After filling with nitrogen, the dried samples were frozen in a refrigerator to give triolein.

HR-EI-MS: m/z=884.7851 (Calcd.=884.7833, $C_{57}H_{104}O_6$), Degree of unsaturation=6.

IR (KBr film):1749, 1165, 1095; 2925, 2854, 723; 3004, 1654 $cm^{-1}$ (weak).

$^1$H-NMR data are shown in Table 8.
$^{13}$C-NMR data are shown in Table 9.

Example 18

Isolation and Identification of 1-Palmitin-2,3-Diolein

Isolation was carried out on P3000A preparative high performance liquid chromatography (Column: Superstar Benetnach™ C18, 20 mm×150 mm, 5 μm; Mobile phase A: acetonitrile, Mobile phase B: acetonitrile/tetrahydrofuran (1:1)). *Coix* seed oil solution was prepared with mobile phase B into 50 mg/mL. Injection volume of each separation was 1.5 mL. Gradient conditions: mobile phase B: 0-27 min: 50%-60%, 27-35 min: 90%, 35-45 min: 100%; Flow rate: 18 mL/min. UV detection wavelength: 208 nm. Peak fractions at retention time of 28.2-29.3 min were collected, and concentrated using a rotary evaporator in vacuum under nitrogen to give crude product.

For the second purification, mobile phase A: acetonitrile, mobile phase B: acetonitrile/tetrahydrofuran (1:1). Solution of the above crude product was prepared with mobile phase B into 20 mg/mL. Injection volume of each separation was 1.5 mL. Column: Superstar Benetnach™ $C_{18}$ (10 mm×250 mm, 5 μm); Gradient conditions: mobile phase B: 0-23 min: 50%-60%, 32-43 min: 60%-90%, 43-60 min: 100%; Flow rate: 3 mL/min; UV detection wavelength: 208 nm. Peak fractions at retention time of 32.9-35.1 min were collected, and concentrated using a rotary evaporator in vacuum under nitrogen. Residues were transferred with chloroform to a 10 mL vial, and dried in a vacuum oven at 35° C. for 6 h. After filling with nitrogen, the dried samples were frozen in a refrigerator to give 1-palmitin-2,3-diolein.

HR-EI-MS: m/z=858.7672 (Calcd.=858.7676, $C_{55}H_{102}O_6$), Degree of unsaturation=5.

IR (KBr film): 1747, 1166, 1095; 2926, 2854, 722; 3003, 1654 cm$^{-1}$ (weak).

$^1$H-NMR data are shown in Table 8.

$^{13}$C-NMR data are shown in Table 9.

Example 19

Preparation of *Coix* Seed Oil Injection of the Invention

Formulation:

| Coix seed oil | 100 g |
| Soybean lecithin for injection | 10 g |
| Glycerin for injection | 15 g |
| Water for injection adds to | 1000 mL | wherein, the *Coix* seed oil contains following ingredients:

| 1,3-diolein | 0.50% |
| 1-linolein-3-olein | 1.31% |
| 1,2-diolein | 0.30% |
| 1-olein-2-linolein | 0.95% |
| 1,2-dilinolein | 0.41% |
| Trilinolein | 6.10% |
| 1-Olein-2,3-dilinolein | 16.18% |
| 1-Palmitin-2,3-dilinolein | 6.56% |
| 1,3-Diolein-2-linolein | 16.69% |
| 1-Palmitin-2-linolein-3-olein | 12.96% |
| 1,3-Dipalmitin-2-linolein | 2.88% |
| Triolein | 18.30% |
| 1-Palmitin-2,3-diolein | 10.18% |

Process:

To a formulated amount of soybean lecithin for injection was added an appropriate amount of water for injection. The mixture was dispersed with a high shear dispersing emulsifier into a dispersion without bulks or granules. Formulated amount of glycerin for injection was added. Then water for injection is added to a specified amount, and the mixture was stirred to give a water phase.

A formulated amount of *Coix* seed oil was weighed. The weighed oil and the water phase prepared above were heated separately to 60, then mixed and emulsified in a high pressure homogenizer, in which the low pressure was 6 MPa and the high pressure was 30 MPa. The homogenization was repeated for 4 times until the amount of particles below 2 μm was no less than 95% and particles above 5 μm were undetectable. If necessary, NaOH or HCl was used to adjust the pH to 8.5.

The resulting homogeneous emulsion was filtered by nitrogen pressure through a microporous filter of 3 μm or less, then filled under nitrogen, and finally sterilized and cooled to afford the injection.

Example 20

Preparation of *Coix* Seed Oil Injection of the Invention

Formulation:

| Coix seed oil | 300 g |
| Soybean lecithin acceptable for injection | 40 g |
| Glycerin acceptable for injection | 50 g |
| Water for injection adds to | 1000 mL | wherein, the *Coix* seed oil contains following ingredients:

| 1,3-diolein | 0.40% |
| 1-linolein-3-olein | 1.05% |
| 1,2-diolein | 0.24% |
| 1-olein-2-linolein | 0.76% |
| 1,2-dilinolein | 0.33% |
| Trilinolein | 4.87% |
| 1-Olein-2,3-dilinolein | 13.00% |
| 1-Palmitin-2,3-dilinolein | 5.25% |
| 1,3-Diolein-2-linolein | 15.13% |
| 1-Palmitin-2-linolein-3-olein | 10.26% |
| 1,3-Dipalmitin-2-linolein | 3.05% |
| Triolein | 20.46% |
| 1-Palmitin-2,3-diolein | 11.50% |

Process:

To a formulated amount of soybean lecithin for injection was added an appropriate amount of water for injection. The mixture was dispersed with a high shear dispersing emulsifier into a dispersion without bulks or granules. Formulated amount of glycerin for injection was added. Then water for injection is added to a specified amount, and the mixture was stirred to give a water phase.

A formulated amount of *Coix* seed oil was weighed. The weighed oil and the water phase prepared above were heated separately to 70, then mixed and emulsified in a high pressure homogenizer, in which the low pressure was 12 MPa and the high pressure was 45 MPa. The homogenization was repeated for 3 times until the amount of particles below 2 μm was no less than 95% and particles above 5 μm were undetectable. If necessary, NaOH or HCl was used to adjust the pH to 7.1.

The resulting homogeneous emulsion was filtered by nitrogen pressure through a microporous filter of 3 μm or less, then filled under nitrogen, and finally sterilized and cooled to afford the injection.

Example 21

Preparation of *Coix* Seed Oil Injection of the Invention

Formulation:

| Coix seed oil | 200 g |
| Soybean lecithin for injection | 25 g |
| Glycerin acceptable for injection | 30 g |
| Water for injection adds to | 1000 mL | wherein, the *Coix* seed oil contains following ingredients:

| 1,3-diolein | 0.45% |
| 1-linolein-3-olein | 1.18% |

| | |
|---|---|
| 1,2-diolein | 0.27% |
| 1-olein-2-linolein | 0.86% |
| 1,2-dilinolein | 0.37% |
| Trilinolein | 5.47% |
| 1-Olein-2,3-dilinolein | 14.75% |
| 1-Palmitin-2,3-dilinolein | 6.01% |
| 1,3-Diolein-2-linolein | 18.19% |
| 1-Palmitin-2-linolein-3-olein | 14.11% |
| 1,3-Dipalmitin-2-linolein | 2.60% |
| Triolein | 16.25% |
| 1-Palmitin-2,3-diolein | 9.11% |

Process:

To a formulated amount of soybean lecithin for injection was added an appropriate amount of water for injection. The mixture was dispersed with a high shear dispersing emulsifier into a dispersion without bulks or granules. Formulated amount of glycerin for injection was added. Then water for injection is added to a specified amount, and the mixture was stirred to give a water phase.

A formulated amount of Coix seed oil was weighed. The weighed oil and the water phase prepared above were heated separately to 65, then mixed and emulsified in a high pressure homogenizer, in which the low pressure was 10 MPa and the high pressure was 30 MPa. The homogenization was repeated for 5 times until the amount of particles below 2 μm was no less than 95% and particles above 5 μm were undetectable. If necessary, NaOH or HCl was used to adjust the pH to 4.8.

The resulting homogeneous emulsion was filtered by nitrogen pressure through a microporous filter of 3 μm or less, then filled under nitrogen, and finally sterilized and cooled to afford the injection.

Example 22

Preparation of Coix Seed Oil Injection of the Invention

Formulation:

| | |
|---|---|
| Coix seed oil | 150 g |
| Soybean lecithin acceptable for injection | 35 g |
| Glycerin acceptable for injection | 30 g |
| Water for injection adds to | 1000 mL | wherein, the Coix seed oil contains following ingredients:

| | |
|---|---|
| 1,3-diolein | 0.49% |
| 1-linolein-3-olein | 1.28% |
| 1,2-diolein | 0.29% |
| 1-olein-2-linolein | 0.93% |
| 1,2-dilinolein | 0.40% |
| Trilinolein | 5.96% |
| 1-Olein-2,3-dilinolein | 15.93% |
| 1-Palmitin-2,3-dilinolein | 6.43% |
| 1,3-Diolein-2-linolein | 16.20% |
| 1-Palmitin-2-linolein-3-olein | 12.57% |
| 1,3-Dipalmitin-2-linolein | 2.79% |
| Triolein | 17.69% |
| 1-Palmitin-2,3-diolein | 9.87% |

Process:

To a formulated amount of soybean lecithin for injection was added an appropriate amount of water for injection. The mixture was dispersed with a high shear dispersing emulsifier into a dispersion without bulks or granules. Formulated amount of glycerin for injection was added. Then water for injection is added to a specified amount, and the mixture was stirred to give a water phase.

A formulated amount of Coix seed oil was weighed. The weighed oil and the water phase prepared above were heated separately to 68, then mixed and emulsified in a high pressure homogenizer, in which the low pressure was 7 MPa and the high pressure was 35 MPa. The homogenization was repeated for 3 times until the amount of particles below 2 μm was no less than 95% and particles above 5 μm were undetectable. If necessary, NaOH or HCl was used to adjust the pH to 6.8.

The resulting homogeneous emulsion was filtered by nitrogen pressure through a microporous filter of 3 μm or less, then filled under nitrogen, and finally sterilized and cooled to afford the injection.

Example 23

Preparation of Coix Seed Oil Capsule of the Invention

Formulation:

| | |
|---|---|
| Coix seed oil | 200 g |
| Vitamine E | 0.20 g |
| to give | 1000 capsules | wherein, the Coix seed oil contains following ingredients:

| | |
|---|---|
| 1,3-diolein | 0.51% |
| 1-linolein-3-olein | 1.34% |
| 1,2-diolein | 0.31% |
| 1-olein-2-linolein | 0.97% |
| 1,2-dilinolein | 0.42% |
| Trilinolein | 6.20% |
| 1-Olein-2,3-dilinolein | 16.58% |
| 1-Palmitin-2,3-dilinolein | 6.69% |
| 1,3-Diolein-2-linolein | 16.87% |
| 1-Palmitin-2-linolein-3-olein | 13.09% |
| 1,3-Dipalmitin-2-linolein | 2.91% |
| Triolein | 18.42% |
| 1-Palmitin-2,3-diolein | 10.27% |

Process:

Glue formulation: Gelatin, purified water, glycerin and 10% ethylparaben solution were weighed at a weight ratio of 1:1.2:0.8:0.01. Glycerin, purified water and 10% ethylparaben solution were sequentially added into a glue melting tank and heated to 70. Then gelatin was added and constantly stirred under vacuum until the gelatin was completely dissolved. The glue was filtered and stored at 60 for use.

Drug liquid formulation: Formulated amount of Coix seed oil and vitamin E were added into an ingredient tank and stirred constantly until thoroughly mixed.

Capsule pressing: Proper pellet dies were chosen according to the capsule size. Capsules were pressed under a tempreture of 18 and a relative humidity of less than 35%, then shaped and dried. After excluding capsules of abnormal size, normal capsules were washed with 95% medicinal ethanol and dried continuously till the moisture content was less than 12%. Unqualified capsules were removed by visual inspection, and the final products were printed and packaged.

Example 24

Preparation of *Coix* Seed Oil Capsule of the Invention

Formulation:

| Coix seed oil | 800 g |
| Tween 80 | 0.60 g |
| to give | 1000 capsules | wherein, the *Coix* seed oil contains following ingredients:

| 1,3-diolein | 0.55% |
| 1-linolein-3-olein | 1.44% |
| 1,2-diolein | 0.33% |
| 1-olein-2-linolein | 1.05% |
| 1,2-dilinolein | 0.45% |
| Trilinolein | 6.69% |
| 1-Olein-2,3-dilinolein | 17.88% |
| 1-Palmitin-2,3-dilinolein | 7.21% |
| 1,3-Diolein-2-linolein | 14.92% |
| 1-Palmitin-2-linolein-3-olein | 11.55% |
| 1,3-Dipalmitin-2-linolein | 3.14% |
| Triolein | 19.86% |
| 1-Palmitin-2,3-diolein | 11.08% |

Process:

Glue formulation: Gelatin, purified water, glycerin and benzoic acid were weighed at a weight ratio of 1:1.2:0.8:0.01. Glycerin, purified water and benzoic acid were sequentially added into a glue melting tank and heated to 90. Then gelatin was added and constantly stirred under vacuum until the gelatin was completely dissolved. The glue was filtered and stored at 56 for use.

Drug liquid formulation: Formulated amount of *Coix* seed oil and Tween 80 were added into an ingredient tank and stirred constantly until thoroughly mixed.

Capsule pressing: Proper pellet dies were chosen according to the capsule size. Capsules were pressed under a tempreture of 26 and a relative humidity of less than 35%, then shaped and dried. After excluding capsules of abnormal size, normal capsules were washed with 95% medicinal ethanol and dried continuously till the moisture content was less than 12%. Unqualified capsules were removed by visual inspection, and the final products were printed and packaged.

Example 25

Preparation of *Coix* Seed Oil Capsule of the Invention

Formulation:

| Coix seed oil | 500 g |
| Vitamine E | 0.40 g |
| to give | 1000 capsules | wherein, the *Coix* seed oil contains following ingredients:

| 1,3-diolein | 0.58% |
| 1-linolein-3-olein | 1.14% |
| 1,2-diolein | 0.35% |
| 1-olein-2-linolein | 0.83% |
| 1,2-dilinolein | 0.47% |
| Trilinolein | 6.99% |
| 1-Olein-2,3-dilinolein | 18.69% |
| 1-Palmitin-2,3-dilinolein | 7.54% |
| 1,3-Diolein-2-linolein | 19.02% |
| 1-Palmitin-2-linolein-3-olein | 14.75% |
| 1,3-Dipalmitin-2-linolein | 3.28% |
| Triolein | 15.96% |
| 1-Palmitin-2,3-diolein | 9.70% |

Process:

Glue formulation: Gelatin, purified water, glycerin and potassium sorbate were weighed at a weight ratio of 1:0.9:0.6:0.005. Glycerin, purified water and potassium sorbate were sequentially added into a glue melting tank and heated to 80. Then gelatin was added and constantly stirred under vacuum until the gelatin was completely dissolved. The glue was filtered and stored at 62 for use.

Drug liquid formulation: Formulated amount of *Coix* seed oil and Vitamine E were added into an ingredient tank and stirred constantly until thoroughly mixed.

Capsule pressing: Proper pellet dies were chosen according to the capsule size. Capsules were pressed under a tempreture of 28 and a relative humidity of less than 35%, then shaped and dried. After excluding capsules of abnormal size, normal capsules were washed with 95% medicinal ethanol and dried continuously till the moisture content was less than 12%. Unqualified capsules were removed by visual inspection, and the final products were printed and packaged.

Example 26

Preparation of *Coix* Seed Oil Capsule of the Invention

Formulation:

| Coix seed oil | 600 g |
| Tween 80 | 0.3 g |
| to give | 1000 capsules | wherein, the *Coix* seed oil contains following ingredients:

| 1,3-diolein | 0.45% |
| 1-linolein-3-olein | 1.26% |
| 1,2-diolein | 0.27% |
| 1-olein-2-linolein | 0.88% |
| 1,2-dilinolein | 0.36% |
| Trilinolein | 6.15% |
| 1-Olein-2,3-dilinolein | 16.31% |
| 1-Palmitin-2,3-dilinolein | 6.66% |
| 1,3-Diolein-2-linolein | 16.77% |
| 1-Palmitin-2-linolein-3-olein | 12.89% |
| 1,3-Dipalmitin-2-linolein | 2.88% |
| Triolein | 18.30% |
| 1-Palmitin-2,3-diolein | 10.18% |

Process:

Glue formulation: Gelatin, purified water, glycerin and chlorhexidine acetate were weighed at a weight ratio of 1:1.0:0.5:0.008. Glycerin, purified water and chlorhexidine acetate were sequentially added into a glue melting tank and heated to 85. Then gelatin was added and constantly stirred under vacuum until the gelatin was completely dissolved. The glue was filtered and stored at 56 for use.

Drug liquid formulation: Formulated amount of *Coix* seed oil and Tween 80 were added into an ingredient tank and stirred constantly until thoroughly mixed.

Capsule pressing: Proper pellet dies were chosen according to the capsule size. Capsules were pressed under a tempreture of 30 and a relative humidity of less than 35%, then shaped and dried. After excluding capsules of abnormal size, normal capsules were washed with 95% medicinal ethanol and dried continuously till the moisture content was less than 12%. Unqualified capsules were removed by visual inspection, and the final products were printed and packaged.

Example 27

Preparation of *Coix* Seed Oil Injection of the Invention

Formulation:

| | |
|---|---|
| Coix seed oil | 100 g |
| Soybean lecithin for injection | 10 g |
| Glycerin for injection | 15 g |
| Water for injection adds to | 1000 mL | wherein, the *Coix* seed oil contains following ingredients:

| | |
|---|---|
| 1,3-diolein | 0.42% |
| 1-linolein-3-olein | 1.25% |
| 1,2-diolein | 0.25% |
| 1-olein-2-linolein | 0.81% |
| 1,2-dilinolein | 0.35% |
| Trilinolein | 5.13% |
| 1-Olein-2,3-dilinolein | 14.09% |
| 1-Palmitin-2,3-dilinolein | 5.74% |
| 1,3-Diolein-2-linolein | 15.01% |
| 1-Palmitin-2-linolein-3-olein | 10.95% |
| 1,3-Dipalmitin-2-linolein | 2.88% |
| Triolein | 20.75% |
| 1-Palmitin-2,3-diolein | 8.69% |

Process:

To a formulated amount of soybean lecithin for injection was added an appropriate amount of water for injection. The mixture was dispersed with a high shear dispersing emulsifier into a dispersion without bulks or granules. Formulated amount of glycerin for injection was added. Then water for injection was added to a specified amount, and the mixture was stirred to give a water phase.

A formulated amount of *Coix* seed oil was weighed. The weighed oil and the water phase prepared above were heated separately to 60, then mixed and emulsified in a high pressure homogenizer, in which the low pressure was 7 MPa and the high pressure was 26 MPa. The homogenization was repeated for 5 times until the amount of particles below 2 μm was no less than 95% and particles above 5 μm were undetectable. If necessary, NaOH or HCl was used to adjust the pH to 6.8.

The resulting homogeneous emulsion was filtered by nitrogen pressure through a microporous filter of 3 μm or less, then filled under nitrogen, and finally sterilized and cooled to afford the injection.

Example 28

Preparation of *Coix* Seed Oil Injection of the Invention

Formulation:

| | |
|---|---|
| Coix seed oil | 300 g |
| Soybean lecithin acceptable for injection | 40 g |
| Glycerin acceptable for injection | 50 g |
| Water for injection adds to | 1000 mL | wherein, the *Coix* seed oil contains following ingredients:

| | |
|---|---|
| 1,3-diolein | 0.46% |
| 1-linolein-3-olein | 1.20% |
| 1,2-diolein | 0.28% |
| 1-olein-2-linolein | 0.90% |
| 1,2-dilinolein | 0.38% |
| Trilinolein | 5.71% |
| 1-Olein-2,3-dilinolein | 15.11% |
| 1-Palmitin-2,3-dilinolein | 6.02% |
| 1,3-Diolein-2-linolein | 15.45% |
| 1-Palmitin-2-linolein-3-olein | 14.20% |
| 1,3-Dipalmitin-2-linolein | 3.20% |
| Triolein | 17.14% |
| 1-Palmitin-2,3-diolein | 9.22% |

Process:

To a formulated amount of soybean lecithin acceptable for injection was added an appropriate amount of water for injection. The mixture was dispersed with a high shear dispersing emulsifier into a dispersion without bulks or granules. Formulated amount of glycerin acceptable for injection was added. Then water for injection is added to a specified amount, and the mixture was stirred to give a water phase.

A formulated amount of *Coix* seed oil was weighed. The weighed oil and the water phase prepared above were heated separately to 70, then mixed and emulsified in a high pressure homogenizer, in which the low pressure was 11 MPa and the high pressure was 48 MPa. The homogenization was repeated for 6 times until the amount of particles below 2 μm was no less than 95% and particles above 5 μm were undetectable. If necessary, NaOH or HCl was used to adjust the pH to 7.5.

The resulting homogeneous emulsion was filtered by nitrogen pressure through a microporous filter of 3 μm or less, then filled under nitrogen, and finally sterilized and cooled to afford the injection.

Example 29

Preparation of *Coix* Seed Oil Injection of the Invention

Formulation:

| | |
|---|---|
| Coix seed oil | 200 g |
| Soybean lecithin for injection | 25 g |
| Glycerin acceptable for injection | 30 g |
| Water for injection adds to | 1000 mL | wherein, the *Coix* seed oil contains following ingredients:

| | |
|---|---|
| 1,3-diolein | 0.50% |
| 1-linolein-3-olein | 1.31% |

-continued

| | |
|---|---|
| 1,2-diolein | 0.30% |
| 1-olein-2-linolein | 0.95% |
| 1,2-dilinolein | 0.41% |
| Trilinolein | 6.18% |
| 1-Olein-2,3-dilinolein | 16.03% |
| 1-Palmitin-2,3-dilinolein | 6.51% |
| 1,3-Diolein-2-linolein | 16.30% |
| 1-Palmitin-2-linolein-3-olein | 12.83% |
| 1,3-Dipalmitin-2-linolein | 2.81% |
| Triolein | 18.10% |
| 1-Palmitin-2,3-diolein | 9.95% |

Process:

To a formulated amount of soybean lecithin for injection was added an appropriate amount of water for injection. The mixture was dispersed with a high shear dispersing emulsifier into a dispersion without bulks or granules. Formulated amount of glycerin acceptable for injection was added. Then water for injection is added to a specified amount, and the mixture was stirred to give a water phase.

A formulated amount of Coix seed oil was weighed. The weighed oil and the water phase prepared above were heated separately to 65, then mixed and emulsified in a high pressure homogenizer, in which the low pressure was 8 MPa and the high pressure was 40 MPa. The homogenization was repeated for 4 times until the amount of particles below 2 μm was no less than 95% and particles above 5 μm were undetectable. If necessary, NaOH or HCl was used to adjust the pH to 6.5.

The resulting homogeneous emulsion was filtered by nitrogen pressure through a microporous filter of 3 μm or less, then filled under nitrogen, and finally sterilized and cooled to afford the injection.

Example 30

Preparation of Coix Seed Oil Capsule of the Invention

Formulation:

| | |
|---|---|
| Coix seed oil | 200 g |
| Vitamine E | 0.20 g |
| to give | 1000 capsules | wherein, the Coix seed oil contains following ingredients:

| | |
|---|---|
| 1,3-diolein | 0.52% |
| 1-linolein-3-olein | 1.40% |
| 1,2-diolein | 0.32% |
| 1-olein-2-linolein | 1.01% |
| 1,2-dilinolein | 0.43% |
| Trilinolein | 6.51% |
| 1-Olein-2,3-dilinolein | 17.26% |
| 1-Palmitin-2,3-dilinolein | 6.84% |
| 1,3-Diolein-2-linolein | 17.65% |
| 1-Palmitin-2-linolein-3-olein | 13.56% |
| 1,3-Dipalmitin-2-linolein | 3.07% |
| Triolein | 19.33% |
| 1-Palmitin-2,3-diolein | 10.80% |

Process:

Glue formulation: Gelatin, purified water, glycerin and 10% ethylparaben solution were weighed at a weight ratio of 1:1.2:0.8:0.01. Glycerin, purified water and 10% ethylparaben solution were sequentially added into a glue melting tank and heated to 70. Then gelatin was added and constantly stirred under vacuum until the gelatin was completely dissolved. The glue was filtered and stored at 59 for use.

Drug liquid formulation: Formulated amount of Coix seed oil and Vitamine E were added into an ingredient tank and stirred constantly until thoroughly mixed.

Capsule pressing: Proper pellet dies were chosen according to the capsule size. Capsules were pressed under a tempreture of 16 and a relative humidity of less than 35%, then shaped and dried. After excluding capsules of abnormal size, normal capsules were washed with 95% medicinal ethanol and dried continuously till the moisture content was less than 12%. Unqualified capsules were removed by visual inspection, and the final products were printed and packaged.

Example 31

Preparation of Coix Seed Oil Capsule of the Invention

Formulation

| | |
|---|---|
| Coix seed oil | 800 g |
| Tween 80 | 0.60 g |
| to give | 1000 capsules | wherein, the Coix seed oil contains following ingredients

| | |
|---|---|
| 1,3-diolein | 0.56% |
| 1-linolein-3-olein | 1.11% |
| 1,2-diolein | 0.34% |
| 1-olein-2-linolein | 0.91% |
| 1,2-dilinolein | 0.46% |
| Trilinolein | 6.71% |
| 1-Olein-2,3-dilinolein | 18.01% |
| 1-Palmitin-2,3-dilinolein | 7.25% |
| 1,3-Diolein-2-linolein | 18.50% |
| 1-Palmitin-2-linolein-3-olein | 11.90% |
| 1,3-Dipalmitin-2-linolein | 2.63% |
| Triolein | 19.91% |
| 1-Palmitin-2,3-diolein | 11.21% |

Process:

Glue formulation: Gelatin, purified water, glycerin and benzoic acid were weighed at a weight ratio of 1:1.2:0.8:0.01. Glycerin, purified water and benzoic acid were sequentially added into a glue melting tank and heated to 90. Then gelatin was added and constantly stirred under vacuum until the gelatin was completely dissolved. The glue was filtered and stored at 60 for use.

Drug liquid formulation: Formulated amount of Coix seed oil and Tween 80 were added into an ingredient tank and stirred constantly until thoroughly mixed.

Capsule pressing: Proper pellet dies were chosen according to the capsule size. Capsules were pressed under a tempreture of 26 and a relative humidity of less than 35%, then shaped and dried. After excluding capsules of abnormal size, normal capsules were washed with 95% medicinal ethanol and dried continuously till the moisture content was less than 12%. Unqualified capsules were removed by visual inspection, and the final products were printed and packaged.

Example 32

Preparation of *Coix* Seed Oil Capsule of the Invention

Formulation:

| | |
|---|---|
| Coix seed oil | 500 g |
| Vitamine E | 0.40 g |
| to give | 1000 capsules | wherein, the *Coix* seed oil contains following ingredients:

| | |
|---|---|
| 1,3-diolein | 0.57% |
| 1-linolein-3-olein | 1.21% |
| 1,2-diolein | 0.34% |
| 1-olein-2-linolein | 0.86% |
| 1,2-dilinolein | 0.46% |
| Trilinolein | 6.85% |
| 1-Olein-2,3-dilinolein | 18.24% |
| 1-Palmitin-2,3-dilinolein | 7.25% |
| 1,3-Diolein-2-linolein | 18.61% |
| 1-Palmitin-2-linolein-3-olein | 12.03% |
| 1,3-Dipalmitin-2-linolein | 3.01% |
| Triolein | 18.60% |
| 1-Palmitin-2,3-diolein | 11.21% |

Process:

Glue formulation: Gelatin, purified water, glycerin and potassium sorbate were weighed at a weight ratio of 1:0.9:0.6:0.005. Glycerin, purified water and potassium sorbate were sequentially added into a glue melting tank and heated to 80. Then gelatin was added and constantly stirred under vacuum until the gelatin was completely dissolved. The glue was filtered and stored at 62 for use.

Drug liquid formulation: Formulated amount of *Coix* seed oil and Vitamine E were added into an ingredient tank and stirred constantly until thoroughly mixed.

Capsule pressing: Proper pellet dies were chosen according to the capsule size. Capsules were pressed under a tempreture of 20 and a relative humidity of less than 35%, then shaped and dried. After excluding capsules of abnormal size, normal capsules were washed with 95% medicinal ethanol and dried continuously till the moisture content was less than 12%. Unqualified capsules were removed by visual inspection, and the final products were printed and packaged.

What is claimed is:

1. A *Coix* seed oil comprising 5 diglyceride and 8 triglyceride ingredients in the following mass percentages: 1,3-diolein 0.40-0.58%, 1-linolein-3-olein 0.91-1.31%, 1,2-diolein 0.24-0.35%, 1-olein-2-linolein 0.66-0.95%, 1,2-dilinolein 0.33-0.47%, trilinolein 4.87-6.99%, 1-olein-2,3-dilinolein 13.00-18.69%, 1-palmitin-2,3-dilinolein 5.25-7.54%, 1,3-diolein-2-linolein 13.23-19.02%, 1-palmitin-2-linolein-3-olein 10.26-14.75%, 1,3-dipalmitin-2-linolein 2.28-3.28%, triolein 14.44-20.76%, and 1-palmitin-2,3-diolein 8.06-11.58%;

wherein, said *Coix* seed oil is prepared by a refining process of crude *Coix* seed oil extracted by supercritical carbon dioxide extraction, said process of the supercritical carbon dioxide extraction comprises steps of:

crushing *Coix* seeds into 10 mesh-80 mesh powder and extracting same using a supercritical $CO_2$ extraction system in which *Coix* seed powder is put in 600 L×2 extractors; the $CO_2$ preheater, extractor and separation column are heated by jacketed circulating hot water to make the extraction temperature and separation temperature reach 33-45° C. and 30-45° C., respectively; the outlet temperatures of separator I and separator II are kept at 20-50° C. and 15-35° C., respectively; the liquid $CO_2$ is pressed at a flow rate of 1-3 t/h into the $CO_2$ preheater via a high pressure pump, turning into a fluid in supercritical state; in the extractor, an oil is extracted into the $CO_2$ fluid at a pressure of 19-23 Mpa; then the $CO_2$ fluid with this oil enters the separation column in which the pressure is controlled to 7-10 Mpa to separate this oil; the $CO_2$ gas out from the separation column enters sequentially into separator I and separator II in which the pressure is sustained at 5-7 Mpa and 4-6 Mpa, respectively; impurities such as water separated therefrom are discarded; the $CO_2$ gas returns to liquid $CO_2$ for reuse through a condenser; and a continuous extraction for 2-3 h affords the crude *Coix* seed oil; and wherein, said refining process comprises steps of:

adding petroleum ether (bp. 60° C.-90° C.) into the *Coix* seed oil obtained by the supercritical $CO_2$ extraction in an amount of 60% of the oil weight; adding 2% NaOH aqueous solution in an amount ranging from 36% to 56% of the oil weight according to the acid value; after stirring the mixture for 10 min and standing for 18-24 h, removing the lower niger layer; washing the upper layer with purified water and letting stand for 18-24 h; after the removal of the lower waste water, washing the upper layer again; after another standing for 40-50 h, removing the lower waste water; and demulsifying the upper layer with acetone in an amount of 70%-90% of the oil weight; after standing for 2-4 h, removing the lower waste acetone and adding 3 to 8% of activated neutral alumina by weight of crude oil in the upper oil layer; stirring the mixture for 30 min, then filtering off the precipitation; heating the filtrate and adding 2% to 6% of activated kaolin by weight of crude oil; stirring the mixture for 30 min at 40-50° C. and then filtering off the precipitation; concentrating the filtrate under a reduced pressure to recover the solvent, then washing again with purified water; after standing for 1-2 h, removing the lower waste water; heating the upper oil layer and vacuum drying it in nitrogen atmosphere; then adding 8%-12% activated neutral alumina, stirring the mixture and allowing to stand at a cold place; after filtration, concentrating the filtrated oil via heating under vacuum in a nitrogen atmosphere and sterilizing the filtrated oil via dry heat sterilization under vacuum at 160-170° C. for 1-2 h; after cooling, filtering the oil through a 0.2 μm microporous membrane; then split charging the obtained *Coix* seed oil in 500 mL glass infusion bottles, nitrogenizing and sealing the bottles.

2. The *Coix* seed oil of claim 1, wherein said 5 diglyceride and 8 triglyceride ingredients are in the following mass percentages: 1,3-diolein 0.45-0.55%, 1-linolein-3-olein 1.03-1.25%, 1,2-diolein 0.27-0.33%, 1-olein-2-linolein 0.75-0.91%, 1,2-dilinolein 0.37-0.45%, trilinolein 5.47-6.69%, 1-olein-2,3-dilinolein 14.63-17.88%, 1-palmitin-2,3-dilinolein 5.90-7.21%, 1,3-diolein-2-linolein 14.88-18.19%, 1-palmitin-2-linolein-3-olein 11.55-14.11%, 1,3-dipalmitin-2-linolein 2.57-3.14%, triolein 16.25-19.86% and 1-palmitin-2,3-diolein 9.07-11.08%.

3. The *Coix* seed oil of claim 1, wherein said 5 diglyceride and 8 triglyceride ingredients are in the following mass percentages: 1,3-diolein 0.49-0.51%, 1-linolein-3-olein 1.12-1.16%, 1,2-diolein 0.29-0.31%, 1-olein-2-linolein 0.81-0.85%, 1,2-dilinolein 0.40-0.42%, trilinolein 5.96-6.20%, 1-olein-2,3-dilinolein 15.93-16.58%, 1-palmitin-2,3-dilinolein 6.43-6.69%, 1,3-diolein-2-linolein 16.20-16.87%, 1-palmitin-2-linolein-3-olein 12.57-13.09%, 1,3-dipalmitin-2-linolein 2.79-2.91%, triolein 17.69-18.42% and 1-palmitin-2,3-diolein 9.87-10.27%.

4. The *Coix* seed oil of claim 1, having the following physicochemical constants based on the fatty oils: specific gravity at 20° C., 0.916-0.920, refractive index at 20° C., 1.471-1.474, acid value <0.2, iodine value 100-106, saponification value 186-195.

5. A pharmaceutical preparation, comprising a therapeutically effective amount of the *Coix* seed oil of claim 1 and one or more pharmaceutically acceptable carriers, wherein said pharmaceutically acceptable carriers are selected from pharmaceutical conventional dilutions, excipients, fillers, emulsifiers, binders, lubricants, absorption accelerators, surfactants, disintegrants, lubricants and antioxidants, if necessary, flavoring agents, sweeteners, preservatives and/or coloring agents.

6. The pharmaceutical preparation of claim 5, wherein said pharmaceutically acceptable carriers are selected from one or more in the group consisting of: mannitol, sorbitol, sodium metabisulfite, sodium bisulfite, sodium thiosulfate, cysteine hydrochloride, thioglycolic acid, methionine, soybean lecithin, vitamin C, vitamin E, EDTA disodium, EDTA calcium sodium, a monovalent alkali metal carbonate, acetate, phosphate or its aqueous solution, hydrochloric acid, acetic acid, sulfuric acid, phosphoric acid, amino acids, sodium chloride, potassium chloride, sodium lactate, ethylparaben solution, benzoic acid, potassium sorbate, chlorhexidine acetate, xylitol, maltose, glucose, fructose, dextran, glycine, starch, sucrose, lactose, mannitol, and silicic derivatives, cellulose and its derivatives, alginates, gelatin, polyvinyl pyrrolidone, glycerin, Tween 80, agar-agar, calcium carbonate, calcium bicarbonate, surfactant, polyethylene glycol, cyclodextrin, β-cyclodextrin, phospholipid material, kaolin, talc, and calcium stearate or magnesium stearate.

7. The pharmaceutical preparation of claim 5, wherein said pharmaceutical preparation is an oral solid preparation, an oral liquid preparation, or an injection.

8. The pharmaceutical preparation of claim 7, wherein:
said oral solid preparation is selected from any one of capsules, tablets, dripping pills, granules, and concentrated pills;
said oral liquid preparation is selected from any one of aqueous or oily suspensions, solutions, emulsions, syrups or elixirs, and a dry product that can be reconstructed by water or other suitable carrier before use; and
said injection is selected from any one of nano suspensions, liposomes, emulsions, lyophilized powder for injection and aqueous injection.

9. The pharmaceutical preparation of claim 7, wherein said injection comprises the following components:

| | |
|---|---|
| Coix seed oil | 50-350 g |
| Soybean lecithin for Injection or soybean lecithin acceptable for injection | 10-40 g |
| Glycerin for Injection or glycerin acceptable for injection | 15-50 g |
| Water for injection adds to | 1000 mL. |

10. The pharmaceutical preparation of claim 9, which is prepared by a method comprising steps of:
adding appropriate amount of water for injection to a formulated amount of soybean lecithin for injection or soybean lecithin acceptable for injection; dispersing the mixture with a high shear dispersing emulsifier to give a dispersion without bulks or granules; adding a formulated amount of glycerin for injection or glycerin acceptable for injection; then adding water for injection to a specified amount, and stirring the mixture to give a water phase;
weighing a formulated amount of *Coix* seed oil; heating the weighed oil and the water phase separately to 60-70° C., then mixing them and emulsifying the mixture in a high pressure homogenizer, in which the low pressure is 5-12 MPa and the high pressure is 25-50 MPa; repeating the cycle of homogenization for 3-6 times until the amount of particles below 2 μm is no less than 95% and particles above 5 μm are undetectable; if necessary, using NaOH or HCl to adjust the pH to 4.8 to 8.5, preferably 6.8 to 7.0, most preferably 6.8; and
filtering the resulting homogeneous emulsion by nitrogen pressure through a microporous filter of 3 μm or less; filling the emulsion, nitrogenizing, sterilizing and cooling to afford the injection.

11. The pharmaceutical preparation of claim 7, wherein said capsule comprises the following components:

| | |
|---|---|
| Coix seed oil | 200-800 g |
| Antioxidant(s) and/or emulsifier(s) | 0.20-0.60 g |
| to give | 1000 capsules. |

12. The pharmaceutical preparation of claim 11, which is prepared by a method comprising steps of:
preparing glue solution: weighing gelatin, purified water, glycerin and a preservative at a weight ratio of 1:0.6-1.2:0.3-0.8:0.0001-0.01; adding glycerin, purified water and preservative sequentially into a glue melting tank; heating to 70° C. -90° C.; then adding gelatin and constantly stirring the mixture under vacuum until the gelatin is completely dissolved; filtering the glue solution and storing the filtered glue solution at 56-62° C. for use;
preparing drug liquid: adding formulated amount of *Coix* seed oil, antioxidant(s) and/or emulsifier(s) into an dosing tank, and stirring the mixture constantly until being homogeneously mixed; and
pressing capsules: choosing proper pellet dies according to the capsule size; pressing capsules in a temperature of 15-30° C. and a relative humidity of less than 35%; drying the pressed and shaped capsules; after removing capsules of abnormal size, washing the normal capsules with 95% medicinal ethanol, and drying them continuously till the moisture content is less than 12%; visually inspecting and removing unqualified capsules; finally printing and packaging to afford the pharmaceutical preparation.

13. The pharmaceutical preparation of claim 12, wherein:
said preservative is selected from any one of 10% ethylparaben solution, benzoic acid, potassium sorbate and chlorhexidine acetate;
said antioxidant is vitamin E; and
said emulsifier is Tween 80.

\* \* \* \* \*